US009364555B2

(12) United States Patent
Floreancig et al.

(10) Patent No.: US 9,364,555 B2
(45) Date of Patent: Jun. 14, 2016

(54) PEDERIN AND PSYMBERIN AGENTS

(75) Inventors: Paul Edward Floreancig, Pittsburgh, PA (US); Billy W. Day, Pittsburgh, PA (US); Shuangyi Wan, Shanghai (CH); Fanghui Wu, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 14/234,133

(22) PCT Filed: Jul. 19, 2012

(86) PCT No.: PCT/US2012/047339
§ 371 (c)(1),
(2), (4) Date: Jan. 21, 2014

(87) PCT Pub. No.: WO2013/016120
PCT Pub. Date: Jan. 31, 2013

(65) Prior Publication Data
US 2014/0161877 A1 Jun. 12, 2014

Related U.S. Application Data

(60) Provisional application No. 61/510,938, filed on Jul. 22, 2011.

(51) Int. Cl.
A61K 47/48 (2006.01)
C07D 407/06 (2006.01)
C07D 407/12 (2006.01)
C07D 407/14 (2006.01)

(52) U.S. Cl.
CPC ........ *A61K 47/48384* (2013.01); *C07D 407/06* (2013.01); *C07D 407/12* (2013.01); *C07D 407/14* (2013.01)

(58) Field of Classification Search
None
See application file for complete search history.

(56) References Cited

FOREIGN PATENT DOCUMENTS

WO    WO 2009/158381    12/2009

OTHER PUBLICATIONS

Hisada et al., "Cytological Effects of Chemicals on Tumors, XXVIII, Notes on the Effect of Extract from Paederus fuscipes on a Transplantable Rat Ascites Tumor", Journal of the Faculty of Science Hokkaido University Series VI, Zoology, 15(4): 684-692, Dec. 1965.*
Vippagunta et al. "Crystalline Solids," Advanced Drug Delivery Reviews, 2001, 48, pp. 18.*
Mailer, Inorganic Structure Chemistry, p. 14-15, 1993.*
CAS Registry Accession No. 58406-71-6 (Entered Nov. 16, 1984).
(Continued)

*Primary Examiner* — Ernst V Arnold
*Assistant Examiner* — Jianfeng Song
(74) *Attorney, Agent, or Firm* — Klarquist Sparkman, LLP

(57) ABSTRACT

Compounds that include a pederin, psymberin or pederin/psymberin chimera scaffold. The pederin scaffold includes a substituent at the C10 and/or C13 position that may include a linker that may be conjugated to a targeting moiety. The psymberin scaffold includes a substituent at the C8 and/or C11 positions that may include a linker that may be conjugated to a targeting moiety. The pederin/psymberin chimera scaffold includes a substituent at the C10 and/or C13 position that may include a linker that may be conjugated to a targeting moiety. The pederin, psymberin or pederin/psymberin chimera scaffold may be modified to include substituents at positions other than the C10 or C13 of pederin, or the C8 and C11 of psymberin.

17 Claims, 3 Drawing Sheets

(56) References Cited

OTHER PUBLICATIONS

International Search Report from parent PCT Application No. PCT/US2012/047339, 4 pages (mailed on Aug. 27, 2012).

Chinen et al. "Irciniastatin A induces JNK activation that is involved in caspase-8-dependent apoptosis via the mitochondrial pathway." *Toxicology Letters*, 199: 341-346, 2010.

Huang et al. "The Discovery of Potent Antitumor Agent C11-Deoxypsymberin/irciniastatin A: Total Synthesis and Biology of Advanced Psymberin Analogs." *Organic Letters*, 11(4): 867-870, 2009.

Jeffrey et al. "Expanded Utility of the β-Glucuronide Linker: ADCs That Deliver Phenolic Cytotoxic Agents." *ACS Med. Chem. Letters*, 1:277-280, 2010.

Lee et al. "Inhibition of protein synthesis and activation of stress-activated protein kinases by onnamide A and theopederin B, antitumor marine natural products." *Cancer Sci.* 96(6): 357-364, 2005.

Ogawara et al. "Change of *ras*-Transformed NRK-Cells Back to Normal Morphology by Mycalamides A and B, Antitumor Agents from a Marine Sponge." *Chem. Pharm. Bull*, 39(8): 2152-2154, 1991.

Richter et al. "The in vitro biological activities of synthetic 18-*O*-methyl mycalamide B, 10-*epi*-18-*O*-methyl mycalamide B and pederin."*Anti-Cancer Drug Design*, 12: 217-227, 1997.

Watanabe et al. "Syntheses and Biological Evaluation of Irciniastatin A and the C1-C2 Alkyne Analogue." *Organic Letters*, 12(5): 1040-1043, 2010.

Wu et al. "Total Synthesis of Pederin and Analogs." *Angew Chem Int Ed Engl* 50(5): 1131-1134, 2011.

Xin et al. "Synthesis of Psymberin Analogs: Probing a Functional Correlation with the Pederin/Mycalamide Family of Natural Products." *Org. Lett.* 9(2): 227-230, 2007.

\* cited by examiner

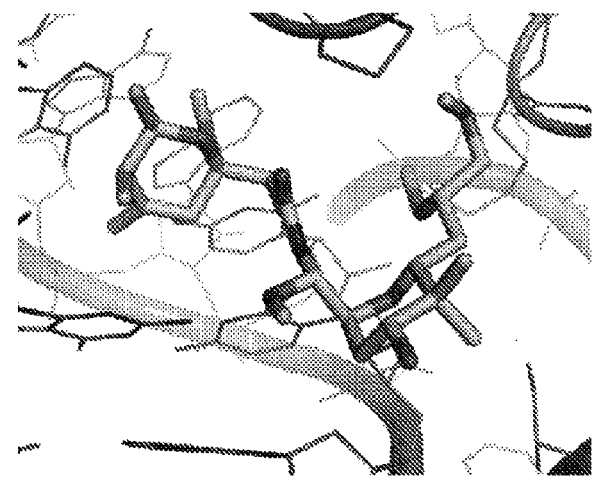
FIG. 2
FIG. 3A
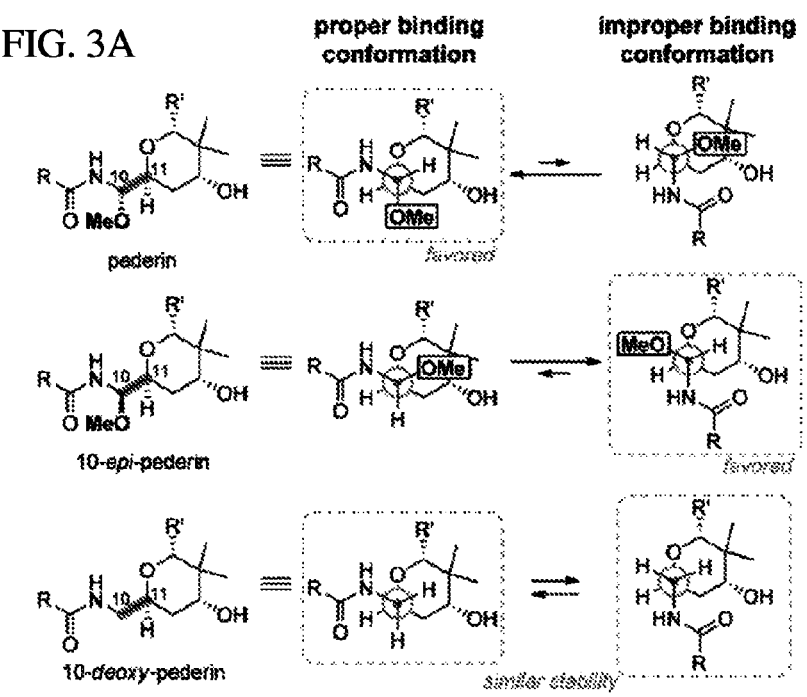
FIG. 3B
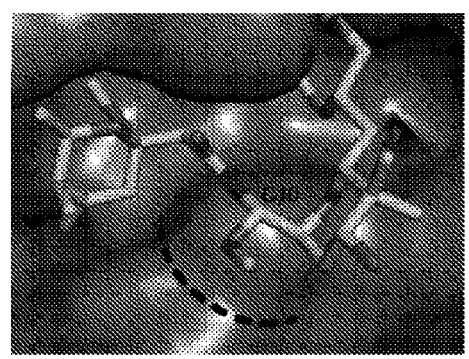
FIG. 3C
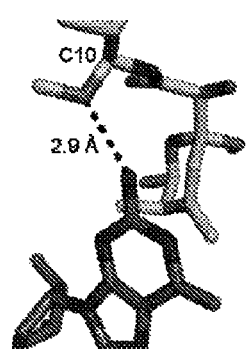

PEDERIN AND PSYMBERIN AGENTS

CROSS REFERENCE TO RELATED APPLICATIONS

This is the U.S. National Stage of International Application No. PCT/US2012/047339, filed Jul. 19, 2012, which was published in English under PCT Article 21(2), which in turn claims the benefit of U.S. Provisional Application No. 61/510,938, filed Jul. 22, 2011. The provisional application is incorporated herein in its entirety.

This invention was made with government support under grant CHE-0848299 awarded by the National Science Foundation. The government has certain rights in the invention.

BACKGROUND

Pederin (1) and psymberin, also known as irciniastatin A, (2) are potent cytotoxins that contain a densely functionalized tetrahydropyran subunit and an N-acyl aminal linkage. These structural features are also found in the mycalamide/theopederin class of molecules, represented by theopederin D (3). Pederin was shown to be a mitotic poison in 1966, but further studies on the biological activity of this family of compounds were not reported until 1989[7] when the mycalamides were identified as potent cytotoxins that showed efficacy in vivo against leukemia and solid tumor models. This study also demonstrated that these compounds are protein synthesis inhibitors. Ogawara and co-workers showed that the mycalamides change ras-transformed cells to normal morphology, and correlated this activity to the inhibition of the synthesis of p21, a cyclin-dependent kinase inhibitor that regulates cell growth (Ogawara et al., Chem. Pharm. Bul. 1991, 39, 2152). The Kocienski group reported that pederin and the mycalamides induce necrosis is squamous carcinoma cells but not in fibroblasts (Richter et al., Anti-Cancer Dru Des. 1997, 12, 217). Further mechanistic work led to the conclusion that these compounds induce apoptosis in a number of cell lines by activating the c-Jun kinase (JNK) and the p31 mitogen-activated protein kinase (Lee et al., Cancer Sci. 2005, 96, 357). Usui and co-workers showed that psymberin induces a similar JNK activation, that the activation is a response to the accumulation of reactive oxygen species in the mitochondria, and that apoptosis is at least partially induced by caspase-8 (Chinen et al, Toxicol. Lett. 2010, 199, 341). Ribosome binding was demonstrated by the displacement of radiolabeled tedanolide from the 60S subunit by pederin, and by the crystal structure of mycalamide A in the ribosomal binding site for the CCA end of tRNAs that occupy the E-site. The interesting biological activity and unique structures of these compounds coupled with their scarcity from natural sources has resulted in a number of total, formal, and partial syntheses of pederin, the mycalamides, and psymberin.

SUMMARY

Disclosed herein in one embodiment is a compound, or a pharmaceutically acceptable salt, ester or solvate thereof, having a formula of:

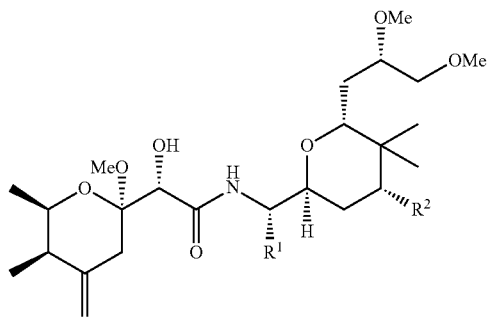

wherein at least one of $R^1$ or $R^2$ includes a linker that includes a reactive functional group that can bind to a targeting moiety; or a formula of:

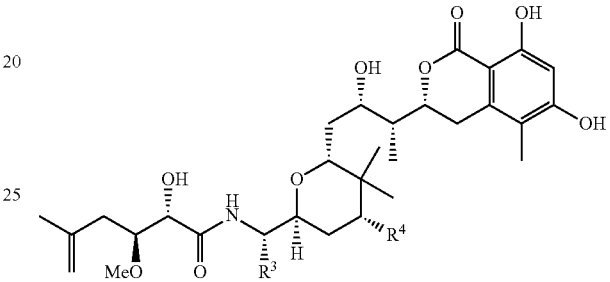

wherein at least one of $R^3$ or $R^4$ includes a linker that includes a reactive functional group that can bind to a targeting moiety; or a formula of:

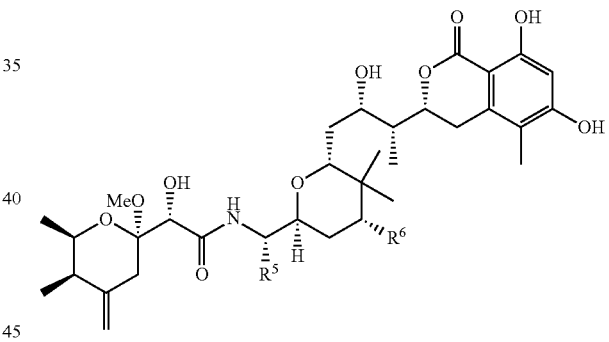

wherein at least one of $R^5$ or $R^6$ includes a linker that includes a reactive functional group that can bind to a targeting moiety.

Another embodiment disclosed herein is a compound, or a pharmaceutically acceptable salt, ester or solvate thereof, having a formula of:

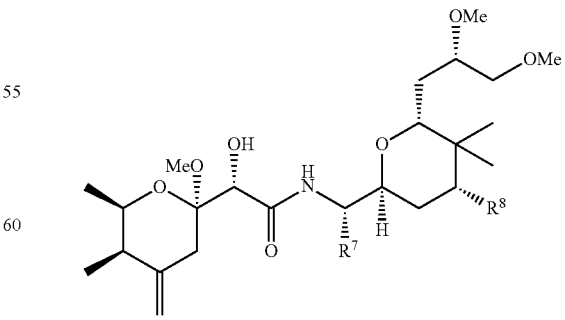

wherein at least one of $R^7$ or $R^8$ includes a structure of -L-T, wherein L is a linker and T is a targeting moiety; or a formula of:

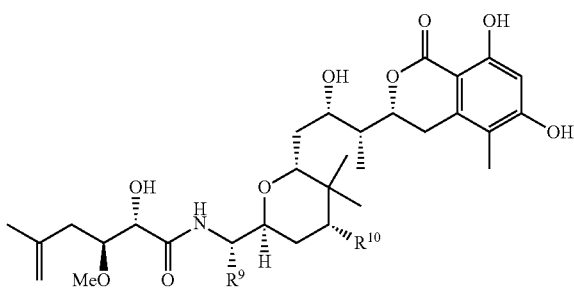

wherein at least one of $R^9$ or $R^{10}$ includes a structure of -L-T, wherein L is a linker and T is a targeting moiety; or a formula of:

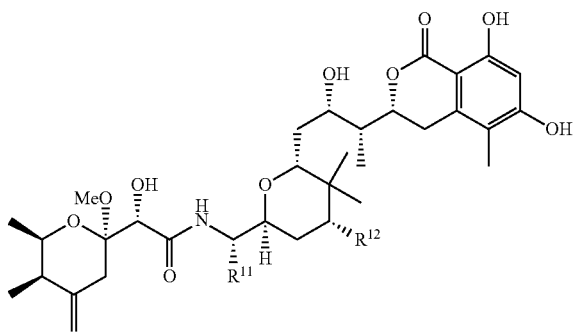

wherein at least one of $R^{11}$ or $R^{12}$ includes a structure of -L-T, wherein L is a linker and T is a targeting moiety.

Further disclosed herein is a compound, or a pharmaceutically acceptable salt, ester or solvate thereof, comprising:

A-L wherein A comprises pederin, a pederin analog, psymberin, a psymberin analog, or a pederin/psymberin chimera; and L comprises a linker that includes a reactive functional group that can bind to a targeting moiety, wherein L is bonded at C10 and/or C13 position of pederin, the pederin analog or the pederin/psymberin chimera, or L is bonded at C8 and/or C11 position of psymberin or the psymberin analog.

Also disclosed herein is a compound, or a pharmaceutically acceptable salt, ester or solvate thereof, having a formula of:

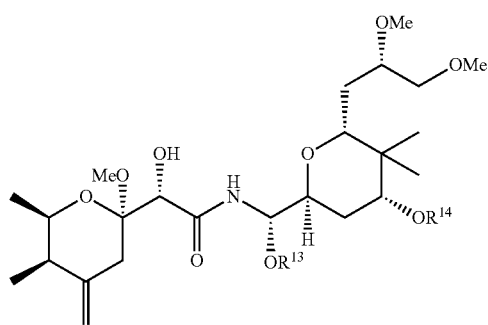

wherein $R^{13}$ is optionally substituted alkyl, and $R^{14}$ is H or optionally substituted alkyl, provided that if $R^{14}$ is H then $R^{13}$ is not methyl; or having a formula of:

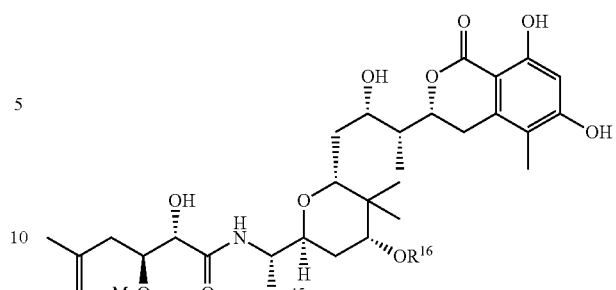

wherein $R^{15}$ is optionally substituted alkyl, and $R^{16}$ is H or optionally substituted alkyl, provided that if $R^{16}$ is H then $R^{15}$ is not methyl; or having a formula of:

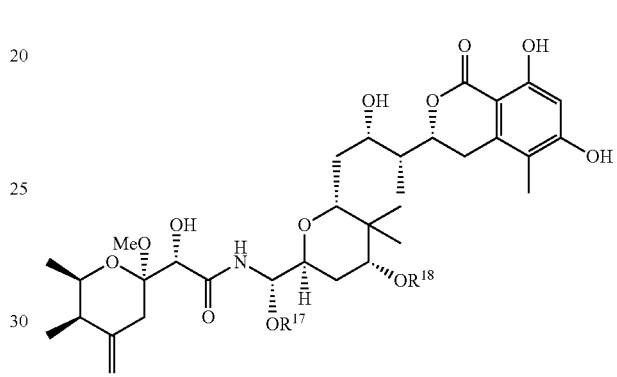

wherein $R^{17}$ is H or optionally substituted alkyl, and $R^{18}$ is H or optionally substituted alkyl.

The foregoing will become more apparent from the following detailed description, which proceeds with reference to the accompanying figures.

BRIEF DESCRIPTION OF THE DRAWINGS

FIG. 2 shows a model of pederin bound to the ribosome.

FIGS. 3A-3C. The C10 methoxy group in pederin plays multiple roles in ribosome binding. (A) The C10 substituent acts as a conformational control element for rotation about the C10-C11 bond; (B) the pederin binding pocket has space to accommodate larger substituents at C10; (C) the C10 oxygen forms a hydrogen-bond to a nearby ribosome nucleobase.

DETAILED DESCRIPTION

Terminology

Figure 1:
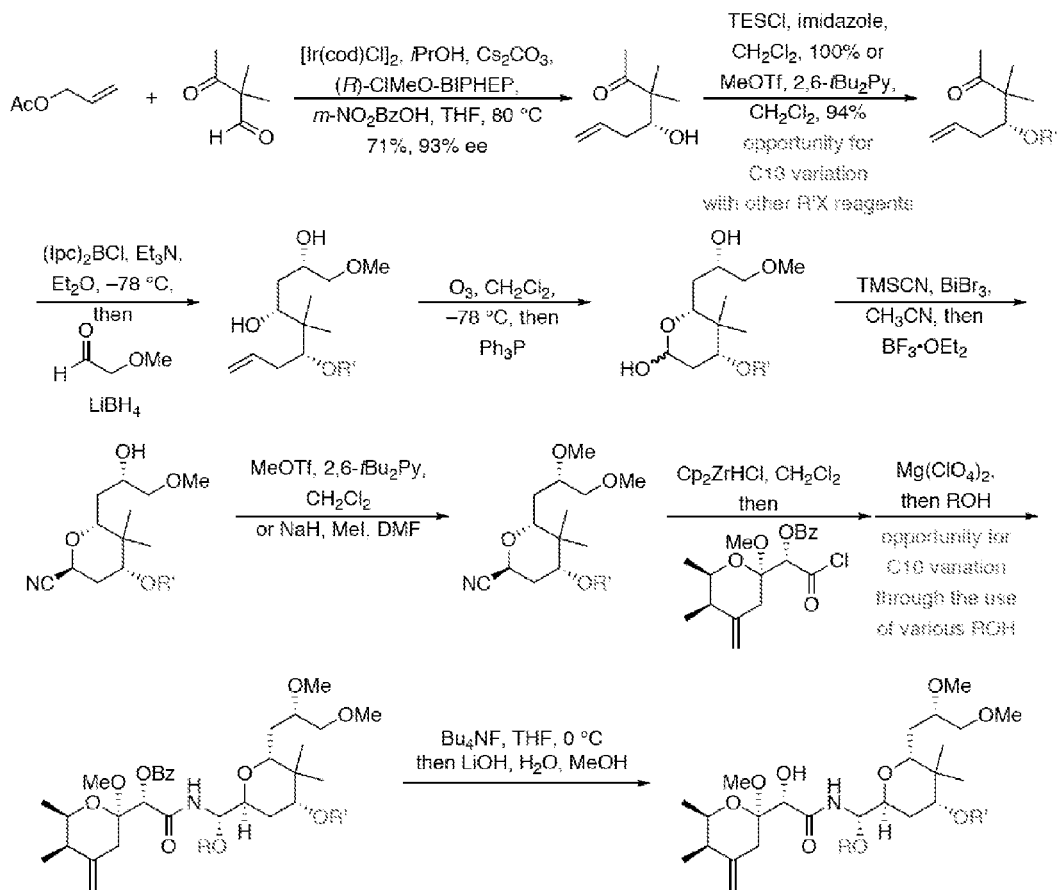
FIG. 1 depicts a synthetic scheme for pederin analogs.

The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

As used herein, the singular terms "a," "an," and "the" include plural referents unless context clearly indicates otherwise. Also, as used herein, the term "comprises" means "includes."

The term "acyl" refers to a group of the formula RC(O)— wherein R is an organic group.

"Administration of" and "administering a" compound should be understood to mean providing a compound, a prodrug of a compound, or a pharmaceutical composition as described herein. The compound or composition can be administered by another person to the subject (e.g., intravenously) or it can be self-administered by the subject (e.g., tablets).

The term "aliphatic" is defined as including alkyl, alkenyl, alkynyl, halogenated alkyl and cycloalkyl groups as described above. A "lower aliphatic" group is a branched or unbranched aliphatic group having from 1 to 10 carbon atoms.

"Alkanediyl," "cycloalkanediyl," "aryldiyl," "alkanearyldiyl" refers to a divalent radical of the general formula —$C_nH_{2n}$— derived from aliphatic, cycloaliphatic, aryl, and alkanearyl hydrocarbons.

The term "alkenyl" refers to a hydrocarbon group of 2 to 24 carbon atoms and structural formula containing at least one carbon-carbon double bond. A "lower alkenyl" group has 1 to 10 carbon atoms.

The term "alkyl" refers to a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 10 carbon atoms. Preferred alkyl groups have 1 to 4 carbon atoms. Alkyl groups may be "substituted alkyls" wherein one or more hydrogen atoms are substituted with a substituent such as halogen, cycloalkyl, alkoxy, amino, hydroxyl, aryl, or carboxyl.

The term "alkyl amino" refers to alkyl groups as defined above where at least one hydrogen atom is replaced with an amino group.

The term "alkylaryl" refers to an aryl group having an alkyl group, as defined above, attached to the aryl group, as defined herein (—Ar—R), wherein Ar is an arylene group and R is an alkyl group.

The term "alkynyl" refers to a hydrocarbon group of 2 to 24 carbon atoms and a structural formula containing at least one carbon-carbon triple bond.

The term "alkoxy" refers to a straight, branched or cyclic hydrocarbon configuration and combinations thereof, including from 1 to 20 carbon atoms, preferably from 1 to 8 carbon atoms, more preferably from 1 to 4 carbon atoms, that include an oxygen atom at the point of attachment. An example of an "alkoxy group" is represented by the formula —OR, where R can be an alkyl group, optionally substituted with an alkenyl, alkynyl, aryl, aralkyl, cycloalkyl, halogenated alkyl, or heterocycloalkyl group as described above. Suitable alkoxy groups include methoxy, ethoxy, n-propoxy, i-propoxy, n-butoxy, i-butoxy, sec-butoxy, tert-butoxy cyclopropoxy, cyclohexyloxy, and the like.

"Alkoxycarbonyl" refers to an alkoxy substituted carbonyl radical, —C(O)OR, wherein R represents an optionally substituted alkyl, aryl, aralkyl, cycloalkyl, cycloalkylalkyl or similar moiety.

The term "amine" or "amino" refers to a group of the formula —NRR', where R and R' can be, independently, hydrogen or an alkyl, alkenyl, alkynyl, aryl, aralkyl, cycloalkyl, halogenated alkyl, or heterocycloalkyl group described above.

"Aminocarbonyl" alone or in combination, means an amino substituted carbonyl (carbamoyl) radical, wherein the amino radical may optionally be mono- or di-substituted, such as with alkyl, aryl, aralkyl, cycloalkyl, cycloalkylalkyl, alkanoyl, alkoxycarbonyl, aralkoxycarbonyl and the like. An aminocarbonyl group may be —N(R)—C(O)—R (wherein R is a substituted group or H) or —C(O)—N(R). An "aminocarbonyl" is inclusive of an amido group. A suitable aminocarbonyl group is acetamido.

The term "amide" or "amido" is represented by the formula —C(O)NRR', where R and R' independently can be a hydrogen, alkyl, alkenyl, alkynyl, aryl, aralkyl, cycloalkyl, halogenated alkyl, or heterocycloalkyl group described above. A suitable amido group is acetamido.

An "animal" refers to living multi-cellular vertebrate organisms, a category that includes, for example, mammals and birds. The term mammal includes both human and non-human mammals. Similarly, the term "subject" includes both human and non-human subjects, including birds and non-human mammals, such as non-human primates, companion animals (such as dogs and cats), livestock (such as pigs, sheep, cows), as well as non-domesticated animals, such as the big cats. The term subject applies regardless of the stage in the organism's life-cycle. Thus, the term subject applies to an organism in utero or in ovo, depending on the organism (that is, whether the organism is a mammal or a bird, such as a domesticated or wild fowl).

An "analog" is a molecule that differs in chemical structure from a parent compound, for example a homolog (differing by an increment in the chemical structure or mass, such as a difference in the length of an alkyl chain or the inclusion of one of more isotopes), a molecular fragment, a structure that differs by one or more functional groups, or a change in ionization. An analog is not necessarily synthesized from the parent compound. Structural analogs are often found using quantitative structure activity relationships (QSAR), with techniques such as those disclosed in Remington (*The Science and Practice of Pharmacology,* 19th Edition (1995), chapter 28). A derivative is a molecule derived from the base structure.

"Antibody" collectively refers to immunoglobulins or immunoglobulin-like molecules (including by way of example and without limitation, IgA, IgD, IgE, IgG and IgM, combinations thereof, and similar molecules produced during an immune response in any vertebrate, for example, in mammals such as humans, goats, rabbits and mice) and antibody fragments that specifically bind to a molecule of interest (or a group of highly similar molecules of interest) to the substantial exclusion of binding to other molecules (for example, antibodies and antibody fragments that have a binding constant, or binding affinity, for the molecule of interest that is at least $10^3$ $M^{-1}$ greater, at least $10^4$ $M^{-1}$ greater or at least $10^5$ $M^{-1}$ greater than a binding constant for other molecules in a biological sample. In one embodiment, binding affinity is calculated by a modification of the Scatchard method described by Frankel et al., *Mol. Immunol.,* 16:101-106, 1979. In another embodiment, binding affinity is measured by an antigen/antibody dissociation rate. In yet another embodiment, a high binding affinity is measured by a competition radioimmunoassay.

The term "antibody" as used herein refers to immunoglobulin molecules and immunologically active portions of immunoglobulin molecules, i.e., molecules that contain an antigen-binding site which specifically binds ("immunoreacts with") an antigen. Structurally, the simplest naturally occurring antibody (e.g., IgG) comprises four polypeptide chains, two heavy (H) chains and two light (L) chains interconnected by disulfide bonds. The immunoglobulins represent a large family of molecules that include several types of molecules, such as IgD, IgG, IgA, IgM and IgE. The term "immunoglobulin molecule" includes, for example, hybrid antibodies, or altered antibodies, and fragments thereof. It has been shown that the antigen binding function of an antibody can be performed by fragments of a naturally-occurring antibody. These fragments are collectively termed "antigen-binding units". Antigen binding units can be broadly divided into "single-chain" ("Sc") and "non-single-chain" ("Nsc") types based on their molecular structures. Antibody covers monoclonal antibodies, polyclonal antibodies, multispecific antibodies (e.g., bispecific antibodies), and antibody fragments.

Also encompassed within the terms "antibody" are immunoglobulin molecules of a variety of species origins including invertebrates and vertebrates. For example, antibodies may be murine, human, humanized, chimeric, or derived from other species. The term "human" as applies to an antibody or an antigen binding unit refers to an immunoglobulin molecule expressed by a human gene or fragment thereof. The term "humanized" as applies to a non-human (e.g. rodent or primate) antibodies are hybrid immunoglobulins, immunoglobulin chains or fragments thereof which contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, rabbit or primate having the desired specificity, affinity and capacity. In some instances, Fv framework region (FR) residues of the human immunoglobulin are replaced by corresponding non-human residues. Furthermore, the humanized antibody may comprise residues which are found neither in the recipient antibody nor in the imported CDR or framework sequences. These modifications are made to further refine and optimize antibody performance and minimize immunogenicity when introduced into a human body. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody may also comprise at least a portion of an immunoglobulin constant region (Fc), typically that of a human immunoglobulin.

"Antigen" refers to a compound, composition, or substance that may be specifically bound by the products of specific humoral or cellular immunity, such as an antibody molecule. Antigens can be any type of molecule including, for example, haptens, simple intermediary metabolites, sugars (e.g., oligosaccharides), lipids, and hormones as well as macromolecules such as complex carbohydrates (e.g., polysaccharides), phospholipids, nucleic acids, proteins, and peptides. Common categories of antigens include, but are not limited to, viral antigens, bacterial antigens, fungal antigens, protozoa and other parasitic antigens, tumor antigens, antigens involved in autoimmune disease, allergy and graft rejection, toxins, and other miscellaneous antigens.

The term "aralkyl" refers to an aryl group having an alkyl group, as defined above, attached to the aryl group, as defined above. An example of an aralkyl group is a benzyl group.

The term "aryl" refers to any carbon-based aromatic group including, but not limited to, benzene, naphthalene, etc. The term "aryl" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorous. The aryl group can be substituted with one or more groups including, but not limited to, alkyl, alkynyl, alkenyl, aryl, halide, nitro, amino, ester, ketone, aldehyde, hydroxy, carboxylic acid, or alkoxy, or the aryl group can be unsubstituted.

"Carbonyl" refers to a radical of the formula —C(O)—. Carbonyl-containing groups include any substituent containing a carbon-oxygen double bond (C=O), including acyl groups, amides, carboxy groups, esters, ureas, carbamates, carbonates and ketones and aldehydes, such as substituents based on —COR or —RCHO where R is an aliphatic, heteroaliphatic, alkyl, heteroalkyl, hydroxyl, or a secondary, tertiary, or quaternary amine.

"Carboxyl" refers to a —COOH radical. Substituted carboxyl refers to —COOR where R is aliphatic, heteroaliphatic, alkyl, heteroalkyl, or a carboxylic acid or ester.

"Conjugate" refers to a molecule comprising two independent molecules, which have been joined through a bond (typically a covalent or ionic bond).

The term "cycloalkyl" refers to a non-aromatic carbon-based ring composed of at least three carbon atoms. Examples of cycloalkyl groups include, but are not limited to, cyclopropyl, cyclobutyl, cyclopentyl, cyclohexyl, and the like. The term "heterocycloalkyl group" is a cycloalkyl group as defined above where at least one of the carbon atoms of the ring is substituted with a heteroatom such as, but not limited to, nitrogen, oxygen, sulfur, or phosphorous.

"Derivative": In chemistry, a derivative is a compound that is derived from a similar compound or a compound that can be imagined to arise from another compound, for example, if one atom is replaced with another atom or group of atoms. The latter definition is common in organic chemistry. In biochemistry, derivative refers to compounds that at least theoretically can be formed from the precursor compound.

The terms "halogenated alkyl" or "haloalkyl group" refer to an alkyl group as defined above with one or more hydrogen atoms present on these groups substituted with a halogen (F, Cl, Br, I).

The term "hydroxyl" is represented by the formula —OH.

The term "hydroxyalkyl" refers to an alkyl group that has at least one hydrogen atom substituted with a hydroxyl group. The term "alkoxyalkyl group" is defined as an alkyl group that has at least one hydrogen atom substituted with an alkoxy group described above.

"Inhibiting" refers to inhibiting the full development of a disease or condition. "Inhibiting" also refers to any quantitative or qualitative reduction in biological activity or binding, relative to a control.

The term "neoplasm" refers to an abnormal cellular proliferation, which includes benign and malignant tumors, as well as other proliferative disorders.

Optionally substituted groups, such as "optionally substituted alkyl," refers to groups, such as an alkyl group, that when substituted, have from 1-5 substituents, typically 1, 2 or 3 substituents, selected from alkoxy, optionally substituted alkoxy, acyl, acylamino, acyloxy, amino, aminoacyl, aminoacyloxy, aryl, carboxyalkyl, optionally substituted cycloalkyl, optionally substituted cycloalkenyl, halogen, optionally substituted heteroaryl, optionally substituted heterocyclyl, hydroxy, sulfonyl, thiol and thioalkoxy. In particular, optionally substituted alkyl groups include, by way of example, haloalkyl groups, such as fluoroalkyl groups, including, without limitation, trifluoromethyl groups.

"Optional" or "optionally" means that the subsequently described event or circumstance can but need not occur, and that the description includes instances where said event or circumstance occurs and instances where it does not.

The terms "pharmaceutically acceptable salt or ester" refers to salts or esters prepared by conventional means that include salts, e.g., of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. "Pharmaceutically acceptable salts" of the presently disclosed compounds also include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, ris(hydroxymethyl)aminomethane, and tetramethylammonium ydroxide. These salts may be prepared by standard procedures, for example by reacting the free acid with a suitable organic or inorganic base. Any chemical compound recited in this specification may alternatively be administered as a pharmaceutically acceptable salt thereof. "Pharmaceutically acceptable salts" are also inclusive of the free acid, base, and zwitterionic forms. Descriptions of suitable pharmaceutically acceptable salts can be found in *Handbook of Pharmaceutical Salts, Properties, Selection and Use*, Wiley VCH (2002). When compounds disclosed herein include an acidic function such as a carboxy group, then suitable pharmaceutically acceptable cation pairs for the carboxy group are well known to those skilled in the art and include alkaline, alkaline earth, ammonium, quaternary ammonium cations and the like. Such salts are known to those of skill in the art. For additional examples of "pharmacologically acceptable salts," see Berge et al., *J. Pharm. Sci.* 66:1 (1977).

"Pharmaceutically acceptable esters" includes those derived from compounds described herein that are modified to include a hydroxy or a carboxyl group. An in vivo hydrolysable ester is an ester, which is hydrolysed in the human or animal body to produce the parent acid or alcohol. Suitable pharmaceutically acceptable esters that include a carboxyl group include $C_{1-6}$ alkoxymethyl esters for example methoxy-methyl, $C_{1-6}$ alkanoyloxymethyl esters for example pivaloyloxymethyl, phthalidyl esters, $C_{3-8}$ cycloalkoxycarbonyloxy, $C_{1-6}$ alkyl esters for example 1-cyclohexylcarbonyl-oxyethyl; 1,3-dioxolen-2-onylmethyl esters for example 5-methyl-1,3-dioxolen-2-onylmethyl; and $C_{1-6}$ alkoxycarbonyloxyethyl esters for example 1-methoxycarbonyl-oxyethyl which may be formed at any carboxy group in the compounds.

An in vivo hydrolysable ester containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxy-methoxy and 2,2-dimethylpropionyloxy-methoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. Examples of substituents on benzoyl include morpholino and piperazino linked from a ring nitrogen atom via a methylene group to the 3- or 4-position of the benzoyl ring.

For therapeutic use, salts of the compounds are those wherein the counterion is pharmaceutically acceptable. However, salts of acids and bases which are non-pharmaceutically acceptable may also find use, for example, in the preparation or purification of a pharmaceutically acceptable compound.

The pharmaceutically acceptable acid and base addition salts as mentioned hereinabove are meant to comprise the therapeutically active non-toxic acid and base addition salt forms which the compounds are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term "addition salt" as used hereinabove also comprises the solvates which the compounds described herein are able to form. Such solvates are for example hydrates, alcoholates and the like.

The term "quaternary amine" as used hereinbefore defines the quaternary ammonium salts which the compounds are able to form by reaction between a basic nitrogen of a compound and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

It will be appreciated that the compounds described herein may have metal binding, chelating, complex forming properties and therefore may exist as metal complexes or metal chelates.

Some of the compounds described herein may also exist in their tautomeric form.

"Preventing" a disease or condition refers to prophylactic administering a composition to a subject who does not exhibit signs of a disease or exhibits only early signs for the purpose of decreasing the risk of developing a pathology or condition, or diminishing the severity of a pathology or condition.

Prodrugs of the disclosed compounds also are contemplated herein. A prodrug is an active or inactive compound that is modified chemically through in vivo physiological action, such as hydrolysis, metabolism and the like, into an active compound following administration of the prodrug to a subject. The term "prodrug" as used throughout this text means the pharmacologically acceptable derivatives such as esters, amides and phosphates, such that the resulting in vivo biotransformation product of the derivative is the active drug as defined in the compounds described herein. Prodrugs preferably have excellent aqueous solubility, increased bioavailability and are readily metabolized into the active inhibitors in vivo. Prodrugs of a compounds described herein may be prepared by modifying functional groups present in the compound in such a way that the modifications are cleaved, either by routine manipulation or in vivo, to the parent compound. The suitability and techniques involved in making and using prodrugs are well known by those skilled in the art. F or a general discussion of prodrugs involving esters see Svensson and Tunek, *Drug Metabolism Reviews* 165 (1988) and Bundgaard, *Design of Prodrugs*, Elsevier (1985).

The term "prodrug" also is intended to include any covalently bonded carriers that release an active parent drug of the present invention in vivo when the prodrug is administered to a subject. Since prodrugs often have enhanced properties relative to the active agent pharmaceutical, such as, solubility and bioavailability, the compounds disclosed herein can be delivered in prodrug form. Thus, also contemplated are prodrugs of the presently disclosed compounds, methods of delivering prodrugs and compositions containing such prodrugs. Prodrugs of the disclosed compounds typically are prepared by modifying one or more functional groups present in the compound in such a way that the modifications are cleaved, either in routine manipulation or in vivo, to yield the parent compound. Prodrugs include compounds having a phosphonate and/or amino group functionalized with any group that is cleaved in vivo to yield the corresponding amino and/or phosphonate group, respectively. Examples of prodrugs include, without limitation, compounds having an acylated amino group and/or a phosphonate ester or phosphonate amide group. In particular examples, a prodrug is a lower alkyl phosphonate ester, such as an isopropyl phosphonate ester.

Protected derivatives of the disclosed compounds also are contemplated. A variety of suitable protecting groups for use with the disclosed compounds are disclosed in Greene and Wuts, *Protective Groups in Organic Synthesis;* 3rd Ed.; John Wiley & Sons, New York, 1999.

In general, protecting groups are removed under conditions which will not affect the remaining portion of the molecule. These methods are well known in the art and include acid hydrolysis, hydrogenolysis and the like. One preferred method involves the removal of an ester, such as cleavage of a phosphonate ester using Lewis acidic conditions, such as in TMS-Br mediated ester cleavage to yield the free phosphonate. A second preferred method involves removal of a protecting group, such as removal of a benzyl group by hydrogenolysis utilizing palladium on carbon in a suitable solvent system such as an alcohol, acetic acid, and the like or mixtures thereof. A t-butoxy-based group, including t-butoxy carbonyl protecting groups can be removed utilizing an inorganic or organic acid, such as HCl or trifluoroacetic acid, in a suitable solvent system, such as water, dioxane and/or methylene chloride. Another exemplary protecting group, suitable for protecting amino and hydroxy functions amino is trityl. Other conventional protecting groups are known and suitable protecting groups can be selected by those of skill in the art in consultation with Greene and Wuts, *Protective Groups in Organic Synthesis;* 3rd Ed.; John Wiley & Sons, New York, 1999. When an amine is deprotected, the resulting salt can readily be neutralized to yield the free amine. Similarly, when an acid moiety, such as a phosphonic acid moiety is unveiled, the compound may be isolated as the acid compound or as a salt thereof.

The term "subject" includes both human and veterinary subjects.

A "therapeutically effective amount" refers to a quantity of a specified agent sufficient to achieve a desired effect in a subject being treated with that agent. Ideally, a therapeutically effective amount of an agent is an amount sufficient to inhibit or treat the disease or condition without causing a substantial cytotoxic effect in the subject. The therapeutically effective amount of an agent will be dependent on the subject being treated, the severity of the affliction, and the manner of administration of the therapeutic composition.

"Treatment" refers to a therapeutic intervention that ameliorates a sign or symptom of a disease or pathological condition after it has begun to develop. As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. The phrase "treating a disease" is inclusive of inhibiting the full development of a disease or condition, for example, in a subject who is at risk for a disease, or who has a disease, such as cancer, particularly a metastatic cancer.

Particular examples of the presently disclosed compounds include one or more asymmetric centers; thus these compounds can exist in different stereoisomeric forms. Accordingly, compounds and compositions may be provided as individual pure enantiomers or as stereoisomeric mixtures, including racemic mixtures. In certain embodiments the compounds disclosed herein are synthesized in or are purified to be in substantially enantiopure form, such as in a 90% enantiomeric excess, a 95% enantiomeric excess, a 97% enantiomeric excess or even in greater than a 99% enantiomeric excess, such as in enantiopure form.

Overview

Pederin and psymberin are structurally related natural products that show potent cytotoxicity against cancer cell lines. Disclosed herein is the synthesis and biological evaluation of these molecules showing that a wide range of substitution is tolerated at the C10 site and a moderate range of substitution is tolerated, and is in some cases beneficial, at the C13 site of pederin. In consideration of the similar structures and modes of action of pederin and psymberin, substitutions at the corresponding sites on psymberin are expected to have a similar impact. The significance of these observations is that the substituents at these sites can contain reactive functional groups that allow for conjugation to drug delivery vehicles such as antibodies, dendrimers, or liposomes. Products that contain these changes are easily prepared through the sequence disclosed herein, making them attractive agents for cancer chemotherapeutic applications in which the general toxicity of the compounds to the organism is mitigated by delivery vehicle, making the anticancer activity highly potent and selective.

Compounds

The compounds disclosed herein include a pederin, psymberin or pederin/psymberin chimera scaffold. The pederin scaffold includes a substituent at the C10 and/or C13 position that may include a linker that may be conjugated to a targeting moiety. The psymberin scaffold includes a substituent at the C8 and/or C11 positions that may include a linker that may be conjugated to a targeting moiety. The pederin/psymberin chimera scaffold includes a substituent at the C10 and/or C13 position that may include a linker that may be conjugated to a targeting moiety. The pederin, psymberin or pederin/psymberin chimera scaffold may be modified to include substituents at positions other than the C10 or C13 of pederin, or the C8 and C11 of psymberin. Examples of the pederin, psymberin and pederin/psymberin compounds are shown below.

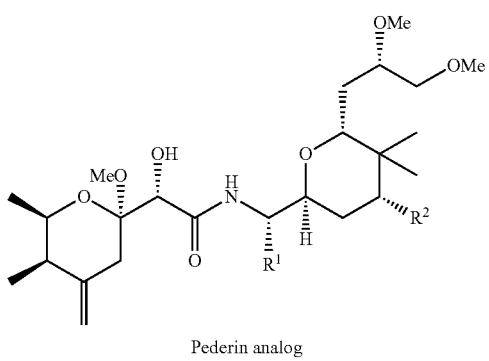

Pederin analog

In certain embodiments, at least one of $R^1$ or $R^2$ includes a linker that includes a reactive functional group that can bond to a targeting moiety. Illustrative linkers and reactive functional groups are described below in more detail. In certain examples, the linker may include a divalent radical such as an alkanediyl, a cycloalkanediyl, an aryldiyl, a heteroaryldiyl, or an alkanearyldiyl. The linker may include at least two divalent radicals coupled to each other, for example, an alkanediyl coupled to a heteroaryldiyl. An illustrative heteroaryldiyl includes a triazolyl divalent radical. In more specific examples, at least one of $R^1$ or $R^2$ has the structure —O-L wherein O is an oxygen atom and L is a linker. In certain embodiments in which $R^1$ includes a linker, $R^2$ is hydroxyl, an alkoxyalkyl, or an alkoxy, particularly hydroxyl or methoxy. In certain embodiments in which $R^2$ includes a linker, $R^1$ is an alkoxy, particularly methoxy.

Also disclosed herein is a compound, or a pharmaceutically acceptable salt, ester or solvate thereof, having a formula of:

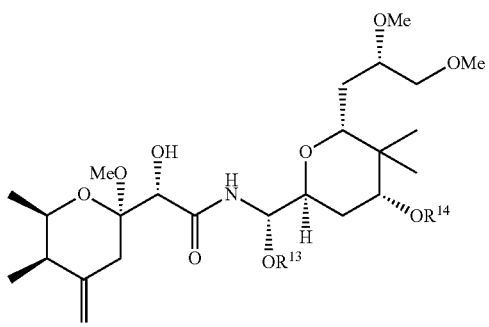

wherein $R^{13}$ is optionally substituted alkyl, and $R^{14}$ is H or optionally substituted alkyl, provided that if $R^{14}$ is H then $R^{13}$ is not methyl. In certain embodiments, $R^{13}$ and $R^{14}$ are each an optionally substituted alkyl. In other embodiments, $R^{13}$ is a substituted alkyl, particularly a lower alkyl, and $R^{14}$ is an alkyl, particularly a lower alkyl. For example, $R^{13}$ is an azide-substituted alkyl, particularly a lower alkyl, and $R^{14}$ is methyl.

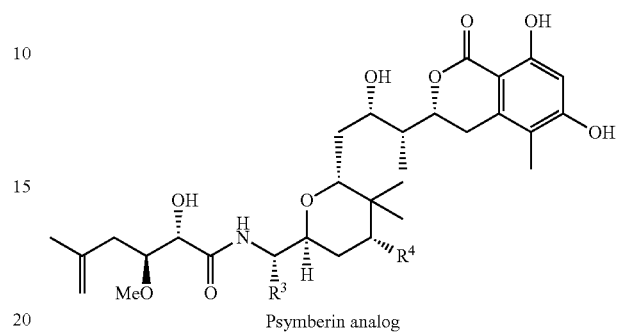

Psymberin analog

In certain embodiments, at least one of $R^3$ or $R^4$ includes a linker that includes a reactive functional group that can bond to a targeting moiety. Illustrative linkers and reactive functional groups are described below in more detail. In certain examples, the linker may include a divalent radical such as an alkanediyl, a cycloalkanediyl, an aryldiyl, a heteroaryldiyl, or an alkanearyldiyl. The linker may include at least two divalent radicals coupled to each other, for example, an alkanediyl coupled to a heteroaryldiyl. An illustrative heteroaryldiyl includes a triazolyl divalent radical. In more specific examples, at least one of $R^3$ or $R^4$ has the structure —O-L wherein O is an oxygen atom and L is a linker. In certain embodiments in which $R^3$ includes a linker, $R^4$ is hydroxyl, an alkoxyalkyl, or an alkoxy, particularly hydroxyl or methoxy. In certain embodiments in which $R^4$ includes a linker, $R^3$ is an alkoxy, particularly methoxy.

Also disclosed herein is a compound, or a pharmaceutically acceptable salt, ester or solvate thereof, having a formula of:

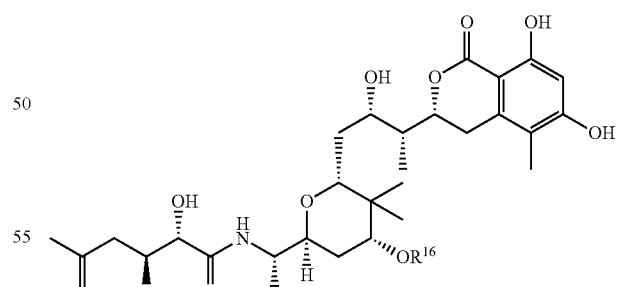

wherein $R^{15}$ is optionally substituted alkyl, and $R^{16}$ is H or optionally substituted alkyl, provided that if $R^{16}$ is H then $R^{15}$ is not methyl. In certain embodiments, $R^{15}$ and $R^{16}$ are each an optionally substituted alkyl. In other embodiments, $R^{15}$ is a substituted alkyl, particularly a lower alkyl, and $R^{16}$ is an alkyl, particularly a lower alkyl. For example, $R^{15}$ is an azide-substituted alkyl, particularly a lower alkyl, and $R^{16}$ is methyl.

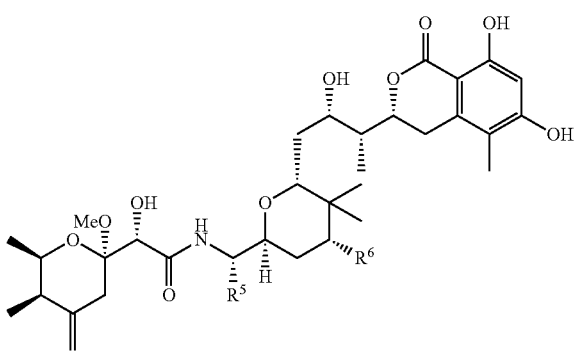

Pederin/psymberin chimera

In certain embodiments, at least one of $R^5$ or $R^6$ includes a linker that includes a reactive functional group that can bond to a targeting moiety. Illustrative linkers and reactive functional groups are described below in more detail. In certain examples, the linker may include a divalent radical such as an alkanediyl, a cycloalkanediyl, an aryldiyl, a heteroaryldiyl, or an alkanearyldiyl. The linker may include at least two divalent radicals coupled to each other, for example, an alkanediyl coupled to a heteroaryldiyl. An illustrative heteroaryldiyl includes a triazolyl divalent radical. In more specific examples, at least one of $R^5$ or $R^6$ has the structure —O-L wherein O is an oxygen atom and L is a linker. In certain embodiments in which $R^5$ includes a linker, $R^6$ is hydroxyl, an alkoxyalkyl, or an alkoxy, particularly hydroxyl or methoxy. In certain embodiments in which $R^6$ includes a linker, $R^5$ is an alkoxy, particularly methoxy.

Also disclosed herein is a compound, or a pharmaceutically acceptable salt, ester or solvate thereof, having a formula of:

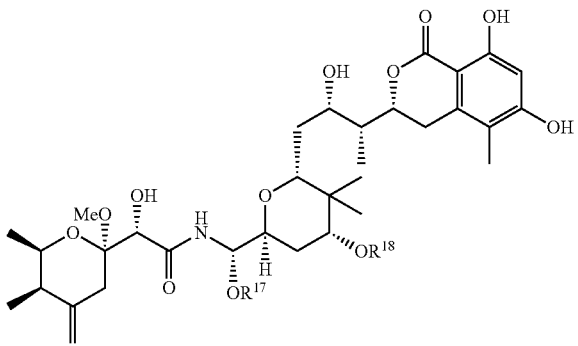

wherein $R^{17}$ is H or optionally substituted alkyl, and $R^{18}$ is H or optionally substituted alkyl. In certain embodiments, $R^{17}$ and $R^{18}$ are each an optionally substituted alkyl. In other embodiments, $R^{17}$ is a substituted alkyl, particularly a lower alkyl, and $R^{18}$ is an alkyl, particularly a lower alkyl. For example, $R^{17}$ is an azide-substituted alkyl, particularly a lower alkyl, and $R^{18}$ is methyl.

Illustrative conjugate compounds that include a targeting moiety are shown below.

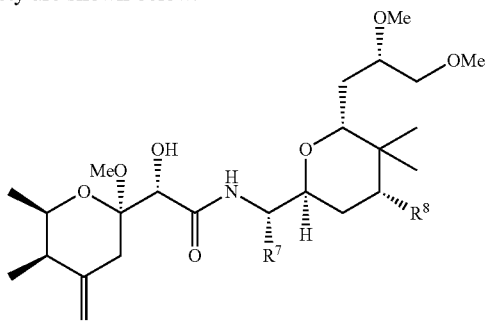

In certain embodiments, at least one of $R^7$ or $R^8$ has a structure that includes -L-T, wherein L is a linker and T is a targeting moiety. In more preferred embodiments, at least one of $R^7$ or $R^8$ has a structure of —O-L-T wherein O is an oxygen atom, L is a linker and T is a targeting moiety. In certain embodiments in which $R^7$ has a structure that includes -L-T, $R^8$ is hydroxyl, an alkoxyalkyl, or an alkoxy, particularly hydroxyl or methoxy. In certain embodiments in which $R^8$ has a structure that includes -L-T, $R^7$ is an alkoxy, particularly methoxy.

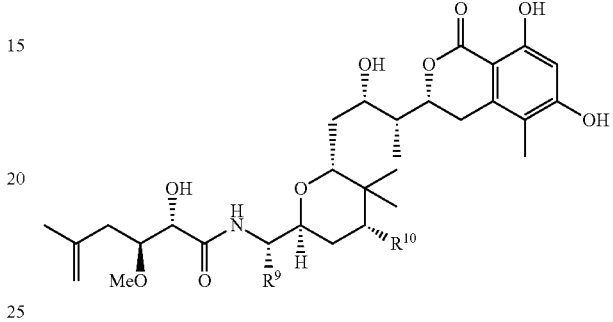

In certain embodiments, at least one of $R^9$ or $R^{10}$ has a structure that includes -L-T, wherein L is a linker and T is a targeting moiety. In more preferred embodiments, at least one of $R^9$ or $R^{10}$ has a structure of —O-L-T wherein O is an oxygen atom, L is a linker and T is a targeting moiety. In certain embodiments in which $R^9$ has a structure that includes -L-T, $R^{10}$ is hydroxyl, an alkoxyalkyl, or an alkoxy, particularly hydroxyl or methoxy. In certain embodiments in which $R^{10}$ has a structure that includes -L-T, $R^9$ is an alkoxy, particularly methoxy.

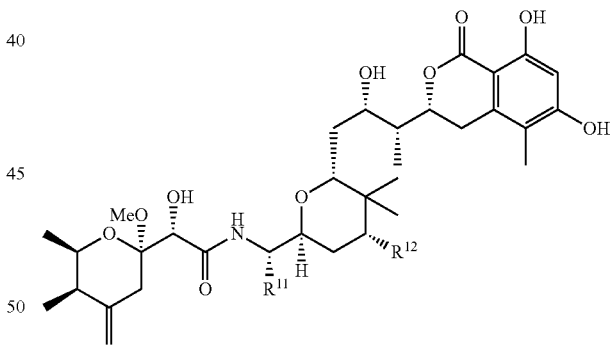

In certain embodiments, at least one of $R^{11}$ or $R^{12}$ has a structure that includes -L-T, wherein L is a linker and T is a targeting moiety. In more preferred embodiments, at least one of $R^{11}$ or $R^{12}$ has a structure of —O-L-T wherein O is an oxygen atom, L is a linker and T is a targeting moiety. In certain embodiments in which $R^{11}$ has a structure that includes -L-T, $R^{12}$ is hydroxyl, an alkoxyalkyl, or an alkoxy, particularly hydroxyl or methoxy. In certain embodiments in which $R^{12}$ has a structure that includes -L-T, $R^{11}$ is an alkoxy, particularly methoxy.

Illustrative examples of compounds that include a linker (benzyldiyl or propanediyl) and a reactive functional group (maleimide) are shown below.

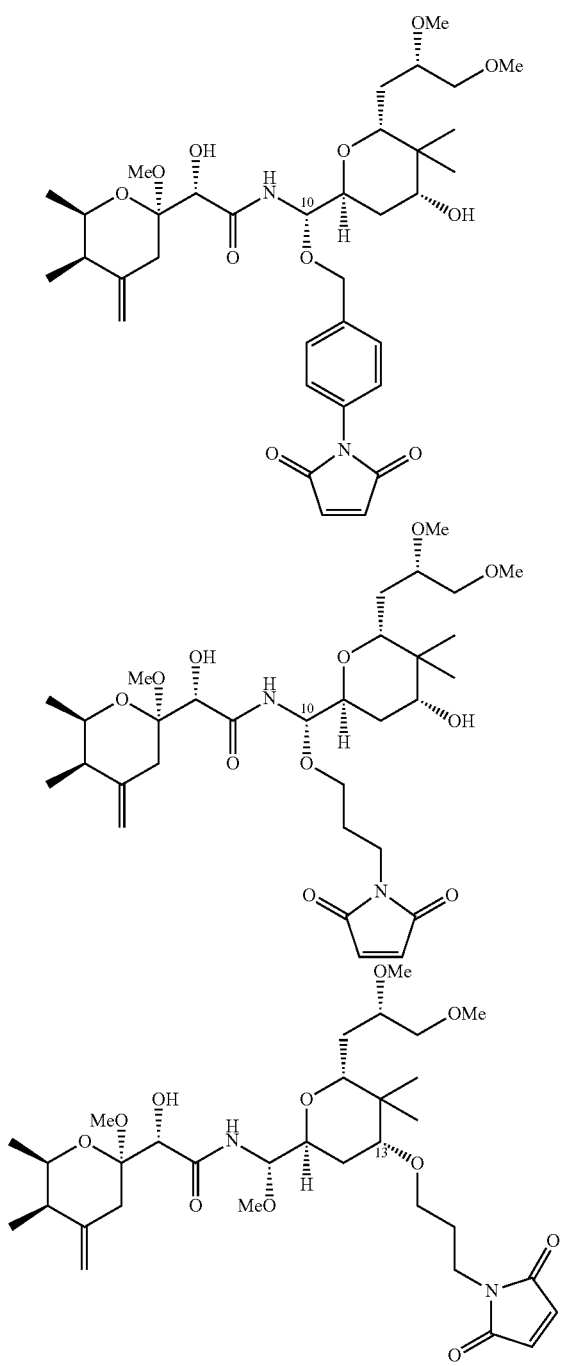

The linker (designated by "-L-" in certain embodiments) may be a covalent bond, a molecule or group of atoms positioned between two moieties (i.e. the pederin or psymberin scaffold and the targeting moiety). Typically, linkers are bifunctional, i.e., the linker includes a functional group at each end, wherein the functional groups are used to couple the linker to the two moieties. The two functional groups may be the same, i.e., a homobifunctional linker, or different, i.e., a heterobifunctional linker. In certain embodiments, the linker is a chemical moiety comprising a covalent bond or a chain of atoms that couples the pederin or psymberin scaffold to a targeting moiety, or covalently attaches the pederin or psymberin scaffold to a targeting moiety. Linkers include, but are not limited to, a divalent radical such as an alkanediyl, a cycloalkanediyl, an aryldiyl, a heteroaryldiyl, moieties such as: —$(CR_2)_nO(CR_2)_n$—, repeating units of alkyloxy (e.g. polyethylenoxy, PEG, polymethyleneoxy) and alkylamino (e.g. polyethyleneamino, Jeffamine®); and diacid ester and amides including maleimide, succinate, succinamide, diglycolate, malonate, and caproamide. Linkers may by derived from linking agents that may be described as including a spacer group and at least two reactive functional groups. Typically, one reactive functional group of the linking agent bonds to a chemical functionality of the pederin or psymberin scaffold, while the other reactive functional group of the linking agent is used to bond to a targeting moiety as described in more detail below.

As mentioned above, the linker of the compounds disclosed herein includes a reactive functional group. In certain embodiments the reactive functional group may be located on a substituted or unsubstituted alkyl, heteroalkyl, alkylaryl, or arylalkyl chain, allowing their facile conjugation to another molecule or agent. A convenient location for the reactive functional group is the terminal position of the linker.

Reactive groups and classes of reactions useful in the presently disclosed compounds may be those that are utilized in the art of bioconjugate chemistry. The reactive functional group may be protected or unprotected, and the protected nature of the group may be changed by methods known in the art of organic synthesis. Illustrative classes of reactions available with reactive cytotoxin analogues are those which proceed under relatively mild conditions. These include, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

Exemplary reaction types include the reaction of carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters. Hydroxyl groups can be converted to esters, ethers, aldehydes, etc. Haloalkyl groups are converted to new species by reaction with, for example, an amine, a carboxylate anion, thiol anion, carbanion, or an alkoxide ion. Dienophile (e.g., maleimide) groups participate in Diels-Alder. Aldehyde or ketone groups can be converted to imines, hydrazones, semicarbazones or oximes, or via such mechanisms as Grignard addition or alkyllithium addition. Sulfonyl halides react readily with amines, for example, to form sulfonamides. Amine or sulfhydryl groups are, for example, acylated, alkylated or oxidized. Alkenes, can be converted to an array of new species using cycloadditions, acylation, Michael addition, etc. Epoxides react readily with amines and hydroxyl compounds.

Illustrative reactive functional groups include, but not limited to, olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Reactive functional groups also include those used to prepare bioconjugates, e.g., N-hydroxysuccinimide esters, maleimides and the like (see, for example, Hermanson, BIOCONJUGATE TECHNIQUES, Academic press, San Diego, 1996). The reactive functional groups may be protected or unprotected.

For example, the reactive functional group might be an amine-reactive group, such as an isothiocyanate, an isocyanate, an acyl azide, an NHS ester, an acid chloride, such as sulfonyl chloride, aldehydes and glyoxals, epoxides and oxiranes, carbonates, arylating agents, imidoesters, carbodiimides, anhydrides, and combinations thereof. Suitable thiol-reactive functional groups include haloacetyl and alkyl halides, maleimides, aziridines, acryloyl derivatives, arylating agents, thiol-disulfide exchange reagents, such as pyridyl disulfides, TNB-thiol, and disulfide reductants, and combinations thereof. Suitable carboxylate-reactive functional groups include diazoalkanes, diazoacetyl compounds, carbonyldiimidazole compounds, and carbodiimides. Suitable hydroxyl-reactive functional groups include epoxides and oxiranes, carbonyldiimidazole, N,N'-disuccinimidyl carbonates or N-hydroxysuccinimidyl chloroformates, periodate oxidizing compounds, enzymatic oxidation, alkyl halogens, and isocyanates. Aldehyde and ketone-reactive functional groups include hydrazines, Schiff bases, reductive amination products, Mannich condensation products, and combinations thereof. Active hydrogen-reactive compounds include diazonium derivatives, mannich condensation products, iodination reaction products, and combinations thereof. Photoreactive chemical functional groups include aryl azides, halogenated aryl azides, benzophonones, diazo compounds, diazirine derivatives, and combinations thereof.

The targeting moiety is the portion of the conjugate disclosed herein that binds, in certain embodiments selectively binds, to a binding partner (i.e. the target of interest). A binding partner may be a molecule or particle which is bound by the targeting moiety. It can be a cell, virus, fragment of a cell, antibody, fragment of an antibody, peptide, protein, polynucleotide, antigen, small molecule, or a combination thereof. The targeting moiety may be of any kind presently known, or that become known and includes peptides and non-peptides. Generally, these can be antibodies (especially monoclonal antibodies), lymphokines, hormones, growth factors, vitamins, nutrient-transport molecules (such as transferrin), or any other cell-binding molecule or substance. More specific examples of targeting moieties that can be used include: polyclonal antibodies; monoclonal antibodies; fragments of antibodies such as Fab, Fab', and F(ab').sub.2, Fv (Parham, J. Immunol. 131:2895-2902 (1983); Spring et al. J. Immunol. 113:470-478 (1974); Nisonoff et al. Arch. Biochem. Biophys. 89:230-244 (1960)); liposomes; dendrimers; interferons (e.g. alpha., .beta., gamma.); lymphokines such as IL-2, IL-3, IL-4, IL-6; hormones such as insulin, TRH (thyrotropin releasing hormone), MSH (melanocyte-stimulating hormone), steroid hormones, such as androgens and estrogens; growth factors and colony-stimulating factors such as EGF, TGF-alpha, FGF, VEGF, G-CSF, M-CSF and GM-CSF (Burgess, Immunology Today 5:155-158 (1984)); transferrin (O'Keefe et al. J. Biol. Chem. 260:932-937 (1985)); and vitamins, such as folate. One preferred targeting moiety is an antibody resulting in an antibody-drug conjugate (ADC) wherein the drug comprises the pederin or psymberin analogs disclosed herein.

In one embodiment, the antibody-drug conjugate includes an antibody, or antibody fragment, that is selected based on its specificity for an antigen expressed on a target cell, or at a target site, of interest. A wide variety of tumor-specific or other disease-specific antigens have been identified and antibodies to those antigens have been used or proposed for use in the treatment of such tumors or other diseases. The antibodies can be used for the treatment of the disease with which the target antigen is associated. Non-limiting examples of target antigens (and their associated diseases) to which an antibody-linker-drug conjugate of the invention can be targeted include: Her2 (breast cancer), CD20 (lymphomas), EGFR (solid tumors), CD22 (lymphomas, including non-Hodgkin's lymphoma), CD52 (chronic lymphocytic leukemia), CD33 (acute myelogenous leukemia), CD4 (lymphomas, autoimmune diseases, including rheumatoid arthritis), CD30 (lymphomas, including non-Hodgkin's lymphoma), Muc18 (melanoma), integrins (solid tumors), PSMA (prostate cancer, benign prostatic hyperplasia), CEA (colorectal cancer), CD11a (psoriasis), CD80 (psoriasis), CD23 (asthma), CD40L (immune thromobcytopenic purpura), CTLA4 (T cell lymphomas) and BLys (autoimmune diseases, including systemic lupus erythematosus).

For preparation of monoclonal or polyclonal antibodies, any technique known in the art can be used (see, e.g., Kohler & Milstein, Nature 256:495-497 (1975); Kozbor et al., Immunology Today 4: 72 (1983); Cole et al., pp. 77-96 in MONOCLONAL ANTIBODIES AND CANCER THERAPY, Alan R. Liss, Inc. (1985)). Methods of production of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to the beta subunits. When appropriately high titers of antibody to the immunogen are obtained, blood is collected from the animal and antisera are prepared. Further fractionation of the antisera to enrich for antibodies reactive to the protein can be done if desired.

Monoclonal antibodies may be obtained by various techniques familiar to those skilled in the art. Briefly, spleen cells from an animal immunized with a desired antigen are immortalized, commonly by fusion with a myeloma cell (see Kohler & Milstein, Eur. J. Immunol. 6: 511-519 (1976)). Alternative methods of immortalization include transformation with Epstein Barr Virus, oncogenes, or retroviruses, or other methods well known in the art.

In certain embodiments, the antibody is a chimeric or humanized antibody. Chimeric or humanized antibodies can be prepared based on the sequence of a murine monoclonal antibody. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art (see e.g., U.S. Pat. No. 5,225,539 to Winter, and U.S. Pat. Nos. 5,530,101; 5,585,089; 5,693,762 and 6,180,370 to Queen et al.).

In another embodiment, the antibody is a human antibody. Such human antibodies can be generated by immunizing transgenic or transchromosomic mice in which the endogenous mouse immunoglobulin genes have been inactivated and exogenous human immunoglobulin genes have been introduced. Such mice are known in the art (see e.g., U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. Nos. 5,939,598; 6,075,181; 6,114,598; 6,150,584 and 6,162,963 to Kucherlapati et al.; and PCT Publication WO 02/43478 to Ishida et al.) Human antibodies can also be prepared using phage display methods for screening libraries of human immunoglobulin genes. Such phage display methods for isolating human antibodies also are known in the art (see e.g., U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.).

The antibody of the antibody-drug conjugates (ADCs) disclosed herein may specifically bind to a receptor encoded by an ErbB gene. The antibody may bind specifically to an ErbB receptor selected from EGFR, HER2, HER3 and HER4. The ADC may specifically bind to the extracellular domain of the HER2 receptor and inhibit the growth of tumor cells which overexpress HER2 receptor. The antibody of the ADC may be a monoclonal antibody, e.g. a murine monoclonal antibody, a chimeric antibody, or a humanized antibody. A humanized antibody may be huMAb4D5-1, huMAb4D5-2, huMAb4D5-3, huMAb4D5-4, huMAb4D5-5, huMAb4D5-6, huMAb4D5-7 or huMAb4D5-8 (Trastuzumab). The antibody may be an antibody fragment, e.g. a Fab fragment.

Known antibodies for the treatment or prevention of cancer can be conjugated as ADC. Antibodies immunospecific for a cancer cell antigen can be obtained commercially or produced by any method known to one of skill in the art such as, e.g., recombinant expression techniques. The nucleotide sequence encoding antibodies immunospecific for a cancer cell antigen can be obtained, e.g., from the GenBank database or a database like it, the literature publications, or by routine cloning and sequencing. Examples of antibodies available for the treatment of cancer include, but are not limited to, humanized anti-HER2 monoclonal antibody for the treatment of patients with metastatic breast cancer; RITUXAN® (rituximab; Genentech) which is a chimeric anti-CD20 monoclonal antibody for the treatment of patients with non-Hodgkin's lymphoma; OvaRex (AltaRex Corporation, MA) which is a murine antibody for the treatment of ovarian cancer; Panorex (Glaxo Wellcome, NC) which is a murine IgG.sub.2a antibody for the treatment of colorectal cancer; Cetuximab Erbitux (Imclone Systems Inc., NY) which is an anti-EGFR IgG chimeric antibody for the treatment of epidermal growth factor positive cancers, such as head and neck cancer; Vitaxin (MedImmune, Inc., MD) which is a humanized antibody for the treatment of sarcoma; Campath I/H (Leukosite, MA) which is a humanized IgG.sub.1 antibody for the treatment of chronic lymphocytic leukemia (CLL); Smart MI95 (Protein Design Labs, Inc., CA) which is a humanized anti-CD33 IgG antibody for the treatment of acute myeloid leukemia (AML); LymphoCide (Immunomedics, Inc., NJ) which is a humanized anti-CD22 IgG antibody for the treatment of non-Hodgkin's lymphoma; Smart ID10 (Protein Design Labs, Inc., CA) which is a humanized anti-HLA-DR antibody for the treatment of non-Hodgkin's lymphoma; Oncolym (Techniclone, Inc., CA) which is a radiolabeled murine anti-HLA-Dr10 antibody for the treatment of non-Hodgkin's lymphoma; Allomune (BioTransplant, CA) which is a humanized anti-CD2 mAb for the treatment of Hodgkin's Disease or non-Hodgkin's lymphoma; Avastin (Genentech, Inc., CA) which is an anti-VEGF humanized antibody for the treatment of lung and colorectal cancers; Epratuzamab (Immunomedics, Inc., NJ and Amgen, CA) which is an anti-CD22 antibody for the treatment of non-Hodgkin's lymphoma; and CEAcide (Immunomedics, NJ) which is a humanized anti-CEA antibody for the treatment of colorectal cancer.

Other antibodies useful in the treatment of cancer include, but are not limited to, antibodies against the following antigens: CA125 (ovarian), CA15-3 (carcinomas), CA19-9 (carcinomas), L6 (carcinomas), Lewis Y (carcinomas), Lewis X (carcinomas), alpha fetoprotein (carcinomas), CA 242 (colorectal), placental alkaline phosphatase (carcinomas), prostate specific antigen (prostate), prostatic acid phosphatase (prostate), epidermal growth factor (carcinomas), MAGE-1 (carcinomas), MAGE-2 (carcinomas), MAGE-3 (carcinomas), MAGE-4 (carcinomas), anti-transferrin receptor (carcinomas), p97 (melanoma), MUC1-KLH (breast cancer), CEA (colorectal), gp100 (melanoma), MART1 (melanoma), PSA (prostate), IL-2 receptor (T-cell leukemia and lymphomas), CD20 (non-Hodgkin's lymphoma), CD52 (leukemia), CD33 (leukemia), CD22 (lymphoma), human chorionic gonadotropin (carcinoma), CD38 (multiple myeloma), CD40 (lymphoma), mucin (carcinomas), P21 (carcinomas), MPG (melanoma), and Neu oncogene product (carcinomas). Some specific, useful antibodies include, but are not limited to, BR96 mAb (Trail, P. A., et al Science (1993) 261, 212-215), BR64 (Trail, P A, et al Cancer Research (1997) 57, 100-105, mAbs against the CD40 antigen, such as S2C6 mAb (Francisco, J. A., et al Cancer Res. (2000) 60:3225-3231), mAbs against the CD70 antigen, such as 1F6 mAb, and mAbs against the CD30 antigen, such as AC10 (Bowen, M. A., et al (1993) J. Immunol., 151:5896-5906; Wahl et al., 2002 Cancer Res. 62 (13):3736-42). Many other internalizing antibodies that bind to tumor associated antigens can be used and have been reviewed (Franke, A. E., et al Cancer Biother Radiopharm. (2000) 15:459-76; Murray, J. L., (2000) Semin Oncol., 27:64-70; Breitling, F., and Dubel, S., Recombinant Antibodies, John Wiley, and Sons, New York, 1998).

Molecular targets for the antibody drug conjugates (ADC) include: (i) tumor-associated antigens; (ii) cell surface receptors, (iii) CD proteins and their ligands, such as CD3, CD4, CD8, CD19, CD20, CD22, CD34, CD40, CD79a and CD79β; (iv) members of the ErbB receptor family such as the EGF receptor, HER2, HER3 or HER4 receptor; (v) cell adhesion molecules such as LFA-1, Mac1, p150,95, VLA-4, ICAM-1, VCAM and αv/β3 integrin including either alpha or beta subunits thereof (e.g. anti-CD11a, anti-CD18 or anti-CD11b antibodies); and (vi) growth factors such as VEGF; IgE; blood group antigens; flk2/flt3 receptor; obesity (OB) receptor; mpl receptor; CTLA-4; protein C, BR3, c-met, tissue factor, β7 etc.

Synthesis

Disclosed herein is a multicomponent acylaminal construction to the total syntheses of pederin, psymberin, and analogs. A synthetic scheme for producing pederin agents is shown in FIG. 1. The synthesis approach provides an opportunity for introducing R' substituents at the C13 position and R substituents at the C10 position of pederin. A linking group that contains a reactive functional group that can bind to a targeting moiety can be introduced as the R' and/or R substituent. For example, a $-(CH_2)_x$-maleimide linking group can be introduced as the R' and/or R substituent. In the case of the R' substituent at the C13 position, a $-(CH_2)_x$-maleimide-containing reagent may be substituted for the TESC1 or MeOTf reactant shown in the scheme of FIG. 1. In the case of the R substituent at the C10 position, a $-(CH_2)_x$-maleimide-containing reagent may be utilized as the ROH reagent. The scheme shown in FIG. 1 is described in more detail below. The corresponding synthesis for psymberin agents is also described in more detail below.

An example of a synthesis of a pederin agent is shown below in Scheme 1. Nitrile 1 was converted to azide 2 through the reaction sequence disclosed herein for the synthesis of pederin and analogs. Base-mediated ester cleavage provided intermediate 3. The azide group was used to couple with N-propargyl maleimide in the presence of CuSO4 to yield maleimide adduct 4. Maleimides are excellent coupling partners to organic thiols and proteins that contain cysteine groups, making 4 a suitable substrate for linkage to a variety of drug delivery vehicles.

Scheme 1

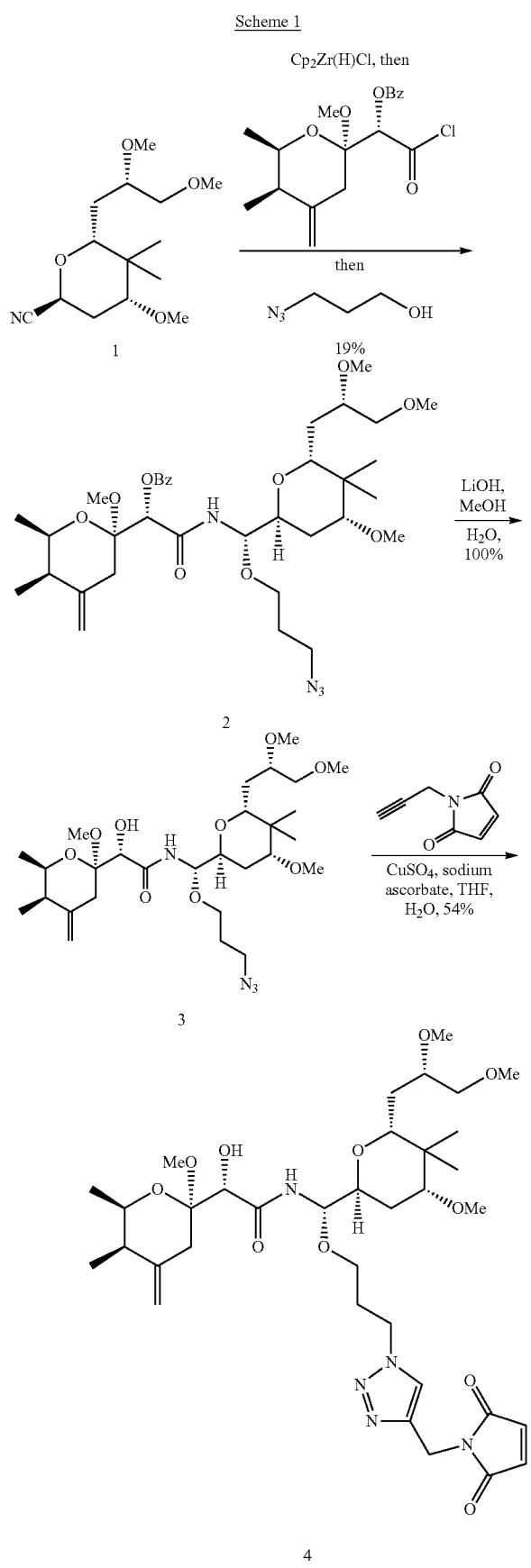

The synthesis of the right fragment of pederin and its analogs is shown in Scheme 2 below. The sequence began with the asymmetric allylation of keto aldehyde 4, prepared on multigram scale from the condensation of acetyl chloride with the morpholine enamine of isobutyraldehyde. Several methods were shown to be successful for this transformation. The Leighton allylation provided superb enantioselectivity and yield, though accessing sufficient quantities of the pseudoephedrine-based reagent for large scale studies proved to be difficult (Kinnaird et al., J. Am. Chem. Soc. 2002, 124, 7920). The abundance of tartaric acid derivatives rendered the Roush allylation a more practical alternative for large scale reactions, though the enantioselectivity was lower and reagent preparation required significant effort (Roush et al, J. Am. Chem. Soc. 1990, 112, 6348). The Krische allylation ultimately provided an ideal solution with respect to reagent availability and reaction enantioselectivity (Kim et al. J. Am. Chem. Soc. 2008, 130, 14891). Exposing 4 to allyl acetate, under the reductive conditions (iPrOH, [Ir(cod)Cl]$_2$, (R)—Cl, MeO-BIPHEP, Cs$_2$CO$_3$, m-NO$_2$BzOH, THF) provided alcohol 5 in 71% yield and 93% ee. Thus the synthesis of a key early stage intermediate that is required for the syntheses of all molecules in this study can be accessed from inexpensive precursors on multigram scale by using asymmetric catalysis. Allylation of the primary alcohol corresponding to 4 was possible under these conditions in the absence of iPrOH, though the overall efficiency from the aldehyde proved to be superior. Conversion of the alcohol to silyl ether 6a, the required intermediate for the total synthesis, and to methyl ether 6b, an intermediate for analog synthesis, proceeded readily under standard conditions. The resulting ketones are well-suited for aldol reactions, and numerous studies have shown that b-alkoxy boron enolates of methyl ketones react with aldehydes to provide good levels of 1,5-asymmetric induction, as required for pederin synthesis. Unfortunately the diastereomeric ratios that we observed for reactions between the dibutylboron or the dicyclohexylboron enolates of 6a and 6b never exceeded 3:1. We therefore explored the pinene-derived boron enolates that were reported by the Paterson group (Paterson et al, Tetrahedron 1990, 46, 4663). These readily prepared compounds substantially enhanced the stereoselectivity of the process to provide product diastereomeric ratios in excess of 15:1. Purification of the product from the pinene-derived by-products proved to be difficult, however, so we exploited the stability of boron chelate 7 to effect a stereoselective reduction with LiBH$_4$. These one flask aldol/reduction reactions provided readily-purified diols 8a and 8b in 80% yield as a single stereoisomer and 78% yield as a 13:1 mixture of stereoisomers, respectively. Although we observed low levels of stereoinduction from the b-substituent and enol diiopinocamphenylborinates from methyl ketones have been shown to react with moderate levels of control, the reenforcing effects led to very satisfying levels of stereocontrol. Ozonolytic alkene cleavage provided lactols 9a and 9b in excellent yield. Cyano group incorporation proceeded without converting the anomeric hydroxyl group to a leaving group or protecting the C17 by ionizing the lactol with BiBr$_3$ in the presence of TMSCN. Yields of nitriles 10a and 10b were low, however, because of the competitive formation of bis-silyl ether 11. No reaction was observed when 11 was isolated and re-subjected to the reaction conditions, indicating that competitively forming the bis-silyl ether limited the efficiency of the process. We reasoned, however, that a stronger Lewis acid would be able to induce ionization of 11. Therefore we added BF$_3$.OEt$_2$ to the reaction mixture after the initial process had occurred. This led to suitable yields of nitriles 12a and 12b. Directly subjecting 10 to BF$_3$.OEt$_2$ and TMSCN led to decomposition, indicating that silyl ether formation through the BiBr$_3$-mediated pathway is a prerequisite to efficient cyanation. Methylation of the secondary alcohols completed the syntheses of multicomponent reaction substrates 13a and 13b. The stereochemical outcomes of these reactions are consistent with Woerpel's studies of cyclic oxocarbenium ion cyanation in acetonitrile (Shenoy et al., J. Am. Chem. Soc. 2006, 128, 8671). Competitive silyl transfer plagued the methylation of 12a under standard Williamson etherification conditions (NaH, DMF, then MeI), causing us to employ MeOTf and di-tert-butylpyridine in $CH_2Cl_2$. The Williamson conditions were appropriate for the more robust substrate 12b.

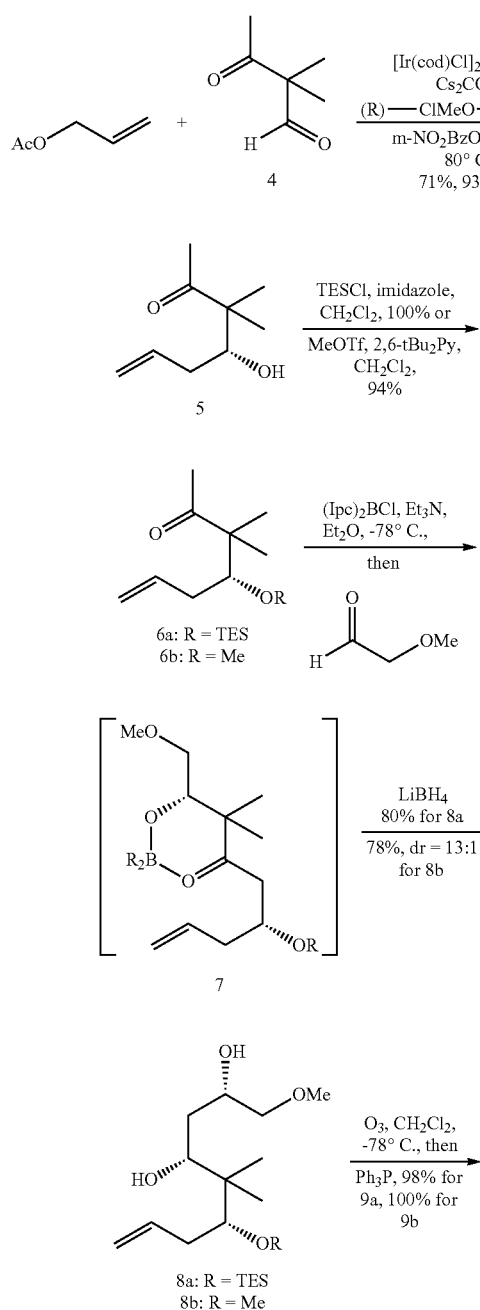

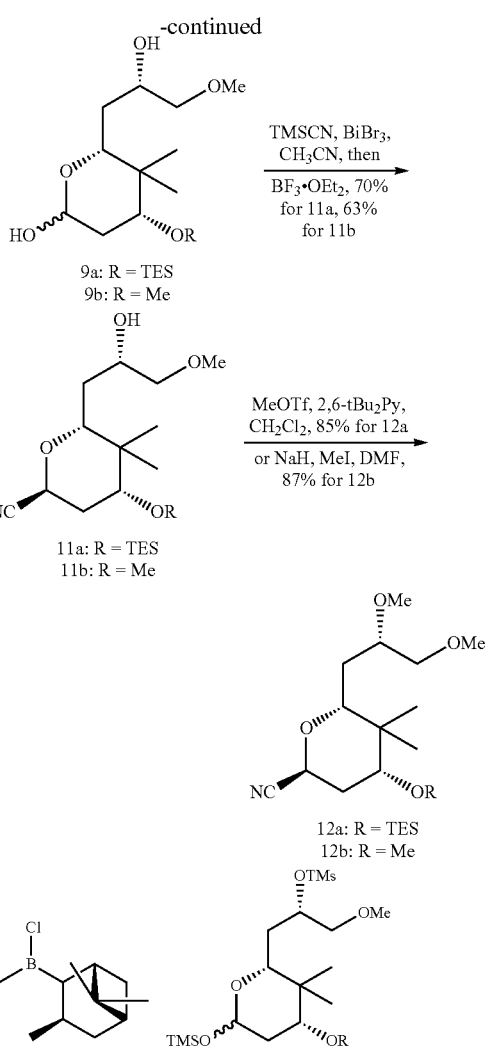

The synthesis of the right-hand fragment for psymberin is shown in Scheme 3 below. An efficient synthesis of this unit requires a rapid construction of the pentasubstituted arene. Rather than modify commercially available arenes, we chose to employ a cycloaddition-based approach to this unit based on work from the Langer group Langer et al., Tetrahedron Lett, 2000, 41, 4545). Thus, allene 13 and diene 14, each available in one step from commercially available sources, were mixed in the absence of solvent to form a cycloadduct that, upon exposure to $Et_3N \cdot HF$, directly yielded 15 in 70% yield. This procedure was very attractive at this point in the synthesis because it could readily be run on large scale. The hydroxyl groups were protected as silyl ethers under standard conditions and the sterically less hindered aliphatic ester group reacted with one equivalent of DIBAL-H to provide aldehyde 16. A Brown crotylation followed by protection of the resulting hydroxyl group as a TBS ether and ozonlytic cleavage of the alkene produced aldehyde 17 (Brown et al, J. Am. Chem. Soc. 1986, 108, 5919). The boron enolate of 6a did not react with 17 smoothly, presumably as a result of enhanced steric hindrance. Therefore we pursued an approach in which the chirality of the aldehyde controls the approach of an enolsilane nucleophile. Applying the Felkin-Anh model to 17 leads to the prediction that nucleophilic addition should provide the desired 1,2-syn-stereochemical relationship (Lodge et al. J. Am. Chem. Soc. 1987, 109, 3353). Evans' polar extended Felkin model, however, predicts that the silyloxy group at the β-position of the aldehyde should guide nucleophiles to produce the undesired 1,3-anti-stereoisomer (Evans et al. Tetrahedron Lett. 1994, 35, 8537). Adding enolsilane 18, prepared in quantitative yield from 6a under standard conditions, to 17 in the presence of BF$_3$.OEt$_2$ produced aldol product 19 in excellent yield as an inseparable 6:1 mixture of diastereomers that favored the syn, syn-stereoisomer. This result was consistent with observations from the Evans group that Felkin-Anh selectivity overrides the induction from β-alkoxy groups when sterically hindered enolsilanes are used as nucleophiles (Evans et al., J. Am Chem. Soc. 2001, 123, 10840). The resulting hydroxy ketone was reduced with NaBH$_4$ and Et$_2$BOMe and provided the expected diol, which could be isolated as a single stereoisomer, with high syn-control as determined by forming the acetonide and analyzing its $^{13}$C NMR spectrum. As in Scheme 2, ozonolysis was employed to form lactol 20. The BiBr$_3$-mediated lactol cyanation conditions from Scheme 2, however, proved to be ineffective in this system and led to substantial decomposition. The strategy of acylating both alcohols and selectively ionizing to yield the tetrahydropyranyl cation worked well, but the subsequent multicomponent reaction was not compatible with the presence of the acetoxy group at C15. The observation that the anomeric hydroxyl group undergoes acylation much faster than the C15 hydroxyl group led us to conduct a selective acylation followed by trimethylsilyl ether formation at C15 to form 21. Cyanation of 21 with BF$_3$.OEt$_2$ provided nitrile 22, but E1 elimination of the intermediate carbocation was competitive. Changing the Lewis acid to TMSOTf, however, provided 22, the key fragment for the multicomponent reaction, in 88% yield.

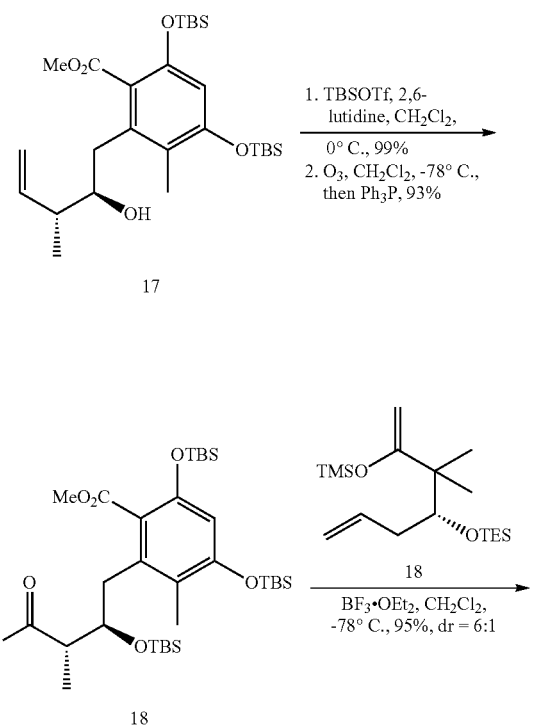

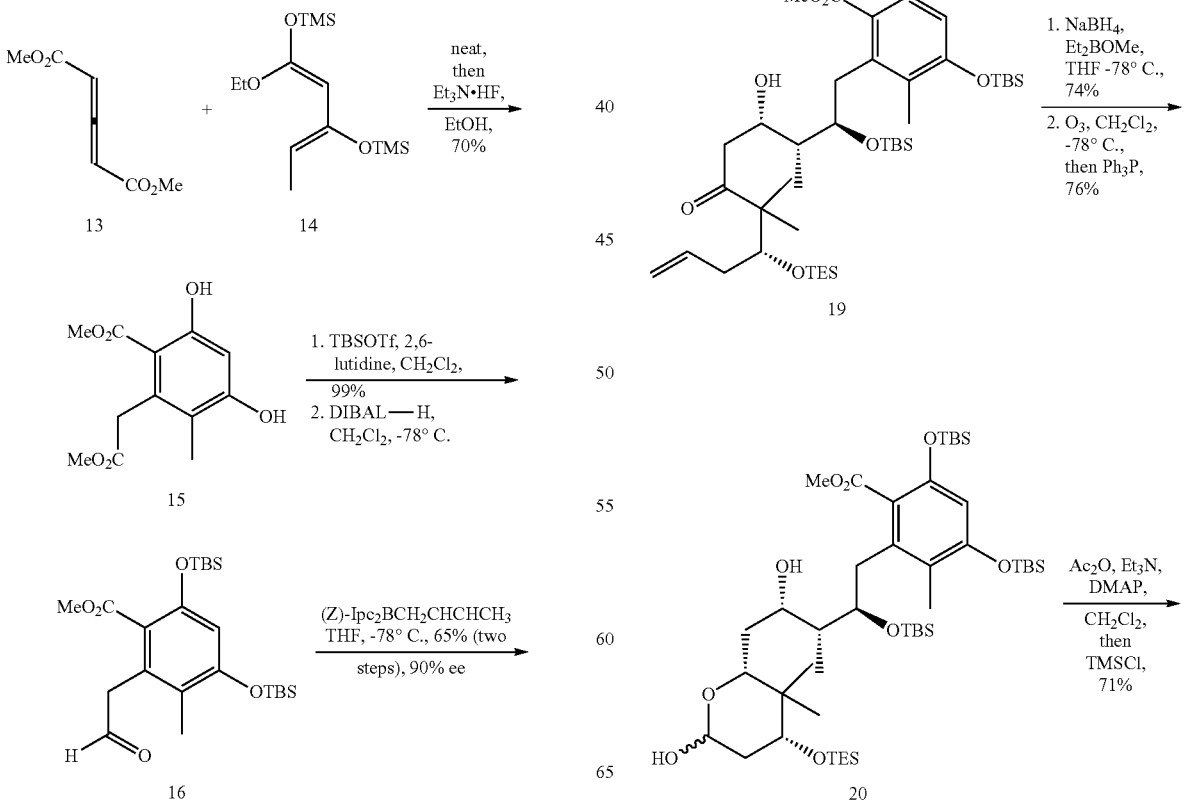

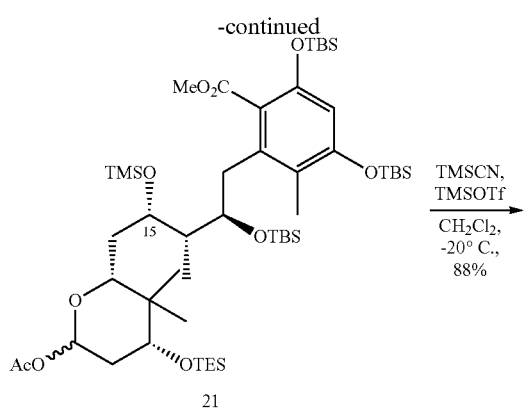

Numerous approaches to the acyl fragment of pederin, in addition to those that were developed for the total syntheses, have been reported. Asymmetry in these sequences invariably arose from the use of chiral reagents or auxiliaries or from chiral pool starting materials. Our objective for the synthesis of this subunit was to develop a route that relies upon asymmetric catalysis to set the absolute stereochemistry. We based our approach (shown in Scheme 4 below) on the route from the Nakata group, in which asymmetric induction arose from the use of an Evans aldol reaction (Breitfelder et al., Helv. Chim. Acta 2004, 87, 1202). β-Lactones are effective surrogates for aldol products that can be prepared enantio- and diastereoselectively through the condensation of aldehydes with acid chlorides in the presence of conchona alkaloid derivatives. Thus acetaldehyde and propionyl chloride were combined in the presence of $Et_3N$, trimethylsilyl quinidine, and $LiClO_4$ to yield a volative β-lactone that was exposed to the lithium enolate of tert-butyl acetate to provide keto ester 23 in 76% yield as a single stereoisomer to the limits of gas chromatographic detection. In accord with Nakata's route, 23 was converted to ester 24 through a sequence of thioacetal formation, stereoselective Claisen condensation with enolate 25 in the presence of $ZnCl_2$, and acidic methanol treatment. Benzoylation, thioacetal cleavage, and methylenation provided benzoylated pederic ester 26. Thiolate mediated cleavage produced acid 27. The presence of the exocyclic alkene in the pederic acid unit causes instability. Therefore we prepared an analog that lacks the alkene. Desulfurization of 24 with Raney nickel followed by benzoylation provided ester 28, which was treated with LiSPr to yield des-methylene pederic acid derivative 29.

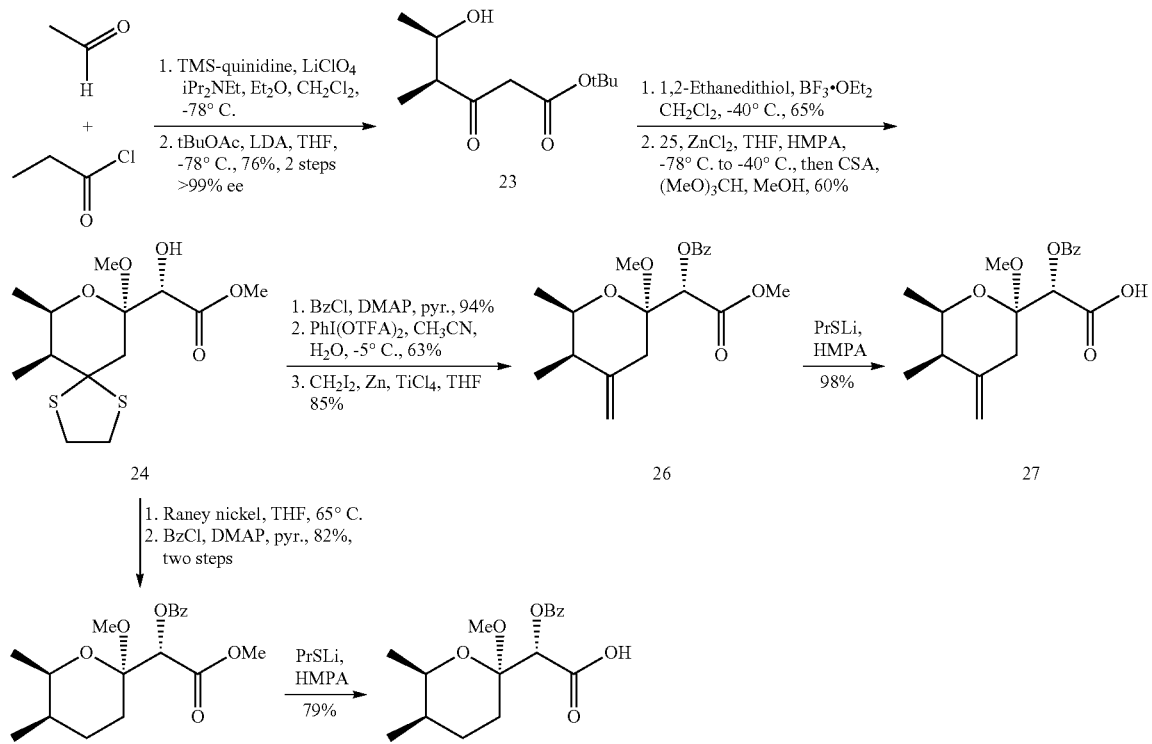

Scheme 4. Synthesis of pederic acid and des-methylene pederic acid.

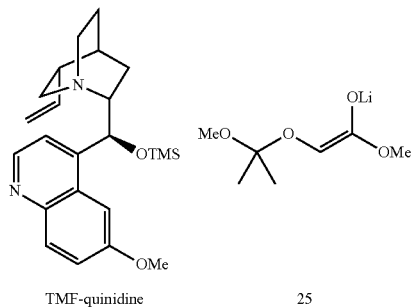

TMF-quinidine 25

The acyl fragment of psymberin (psymberic acid) has also been prepared through several approaches. In consideration of our desire to minimize late stage deprotection efforts we employed Pietruszka's route (Scheme 5 below) that is based on a stereoselective aldol reaction between β,γ-unsaturated aldehyde 30 and glycolic acid acetal 31 (Pietruszka et al. Eur. J. Org. Chem. 2009, 3628). This route provided abundant quantities of acid 32 in which the hydroxyl group at C5 was protected as a benzoate ester, in accord with our projected final deprotection strategy.

Scheme 5. Synthesis of psymberic acid.

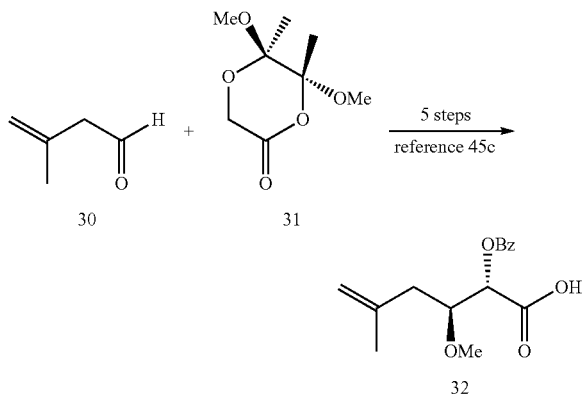

The fragment coupling in the pederin series is shown in Scheme 6. Hydrozirconation of nitrile 12a with $Cp_2Zr(H)Cl$ followed by the addition of acid chloride 33, freshly prepared from 27 prior to the reaction and used without purification, resulted in the transient formation of acylimine 34. The addition was conducted at −78° C. due to the propensity of 34 to undergo tautomerization to form a stable enamide product. The observation of tautomerization as a competitive process was not observed in simpler systems, even when a tetrahydropyranyl nitrile was used as the substrate (Wan et al. Org Lett. 2007, 9, 5385). Adding structurally simpler acid chlorides to the hydrozirconation product of 12a also promoted the formation enamide products, indicating that tautomerization can be attributed to structural elements in the nitrile component. $Mg(ClO_4)_2$ was added to lock the acylimine conformation by chelation between the nitrogen of the imine and the oxygen of the tetrahydropyran, thereby promoting nucleophilic attack through the desired, less hindered trajectory. Alcohol addition led to the desired acyl aminals 35a-d. Ethanol and trifluoroethanol were selected as nucleophiles to determine whether the ease of acyl aminal ionization, a proposed mechanism of action for these species, would cause a difference in biological activity for structurally similar species. Dimethoxybenzyl alcohol was selected because it provides potential access to the acyl hemiaminal analog that should be a biosynthetic precursor to pederin and because the final product will provide information on the tolerance of the bonding site for larger groups that could provide useful handles for probe development. The yields for these reactions were moderate but the stereocontrol was good to excellent and products were readily isolated in sufficient quantities to complete the syntheses and conduct biological evaluations. Reduction of acylimine 34 by residual $Cp_2Zr(H)Cl$ to form amide 35e was a side reaction in each of these reactions, allowing us to accrue sufficient quantities of the amide for subsequent studies. The syntheses of pederin and analogs were completed by a one flask protocol that was inspired by Rawal's synthesis whereby silyl group cleavage was effected by $Bu_4NF$ in THF followed by the addition of aqueous LiOH and MeOH to cleave the benzoate ester (Jewett et al., Angew. Chem., Int. Ed. 2007, 46, 6502). Pederin (1) and analogs 36b-e were prepared through this route. The efficiency of the process was high for all substrates except 35c, in which the basic conditions promoted the elimination of the trifluoroethoxy group to form enamide analog 37 in 29% yield as a side product. The longest linear step count for these syntheses was 10 steps.

Scheme 6. Synthesis of pederin and acyl aminal analogs.

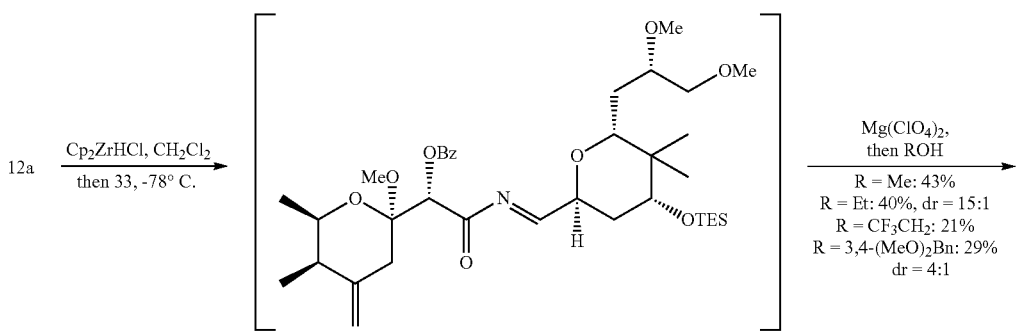

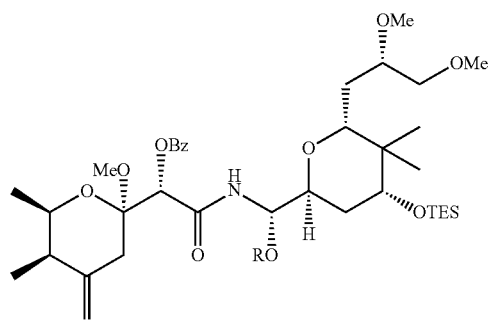
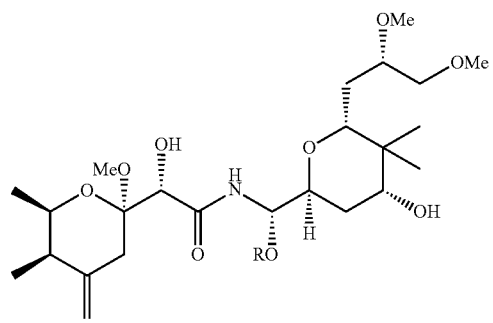

35
a: R = Me
b: R = Et
c: R = CF$_3$CH$_2$
d: R = 3,4-(MeO)$_2$Bn

1: R = Me
36b: R = Et
36c: R = CF$_3$CH$_2$
36d R = 3,4-(MeO)$_2$Bn

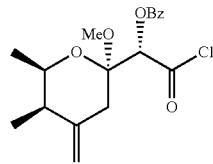
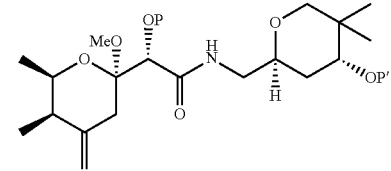
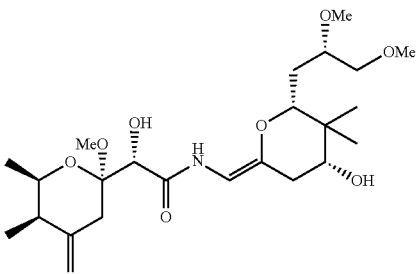

33

35e: P = Bz, P′ = TES
36e: R, P′ = H

37

Through related sequences (Scheme 7) 12a was coupled with acid chloride 39, prepared from 29 immediately prior to coupling, to form des-methylene pederin analog 40. Nitrile 12b was converted to methyl ether analog 41. The syntheses of these analogs demonstrates late stage that the multicomponent assembly of the acyl aminal group can be used to introduce structural variations in all sections of the natural product, thereby greatly facilitating structure-activity relationship studies.

Scheme 7. Variations in the left and right fragments of pederin.

12a
1. Cp$_2$Zr(H)Cl, CH$_2$Cl$_2$, then 39, -78° C., then Mg(ClO$_4$)$_2$, MeOH, 35%
2. Bu$_4$NF, THF, then LiOH MeOH, H$_2$O, 82%
→

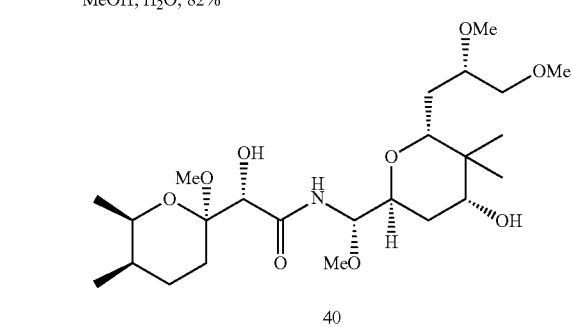

40

12b
1. Cp$_2$Zr(H)Cl, CH$_2$Cl$_2$, then 33, -78° C., then Mg(ClO$_4$)$_2$, MeOH, 30%
2. LiOH, MeOH, H$_2$O, 80%
→

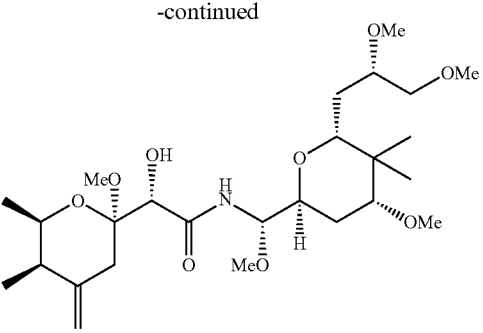

41

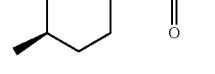

39

The multicomponent approach to the acyl aminal of psymberin proved to be much more challenging than the corresponding reaction in the pederin series. Difficulties in controlling the stereochemical outcome of the reaction could be predicted based on De Brabander's approach to a pederin/psymberin hybrid structure in which the approach of NaBH$_4$ to acylated imidate intermediates that are structurally related to the acylimines in our procedure proceeded with opposite trajectories for the pederin and psymberin subunits (Xiang et al., Org. Lett. 2007, 9, 227). The results disclosed herein provide further evidence that remote interactions can exert a strong influence over the reactivity at the acyl aminal site.

Exposing nitrile 22 to $Cp_2Zr(H)Cl$, acyating with acid chloride 42, and adding MeOH provided diastereomeric acyl aminals 43 and 44, in a 1:3 ratio in which the desired stereoisomer was the desired product. Adding one equivalent of $Mg(ClO_4)_2$ improved the ratio to 1:2. Increasing the equivalents of $Mg(ClO_4)_2$ incrementally increased the stereocontrol, with 2 eq providing a 1:1 ratio and 10 eq leading to a 3:1 ratio, albeit at the expense of the overall efficiency of the reaction. We hypothesized that replacing MeOH with a less reactive or bulkier surrogate would improve the stereoselectivity. Conducting the addition with 2 eq $Mg(ClO_4)_2$ and $(MeO)_3CH$ as the source of the methoxy group provided a 3:1 mixture of 43 and 44, as determined by crude NMR. For simplicity the crude mixture was carried to the next step without purification. Exposing the acyl aminal mixture to $Bu_4NF$ in DMF led to the cleavage of all silyl groups, formation of the dihydroisocoumarin, and cleavage of the benzoate to yield psymberin in 18% yield for the two steps. The benzoate cleavage most likely resulted from the generation of $Bu_4NOH$ during the cleavage of the silyl ethers. The identity of the protecting group at C15 proved to be critical for the success of this transformation. Cleavage at of the silyl ether at C17 was not observed when the C15 oxygen was protected as an acetate or a bulkier silyl ether. We postulate that the cleavage of the labile C15 TMS ether allows for intramolecular silyl transfer from C17. Cleavage of the resulting C17 silyl ether then leads to the final product. Thus psymberin is available from commercially available materials through a route that is only 14 steps in its longest linear sequence.

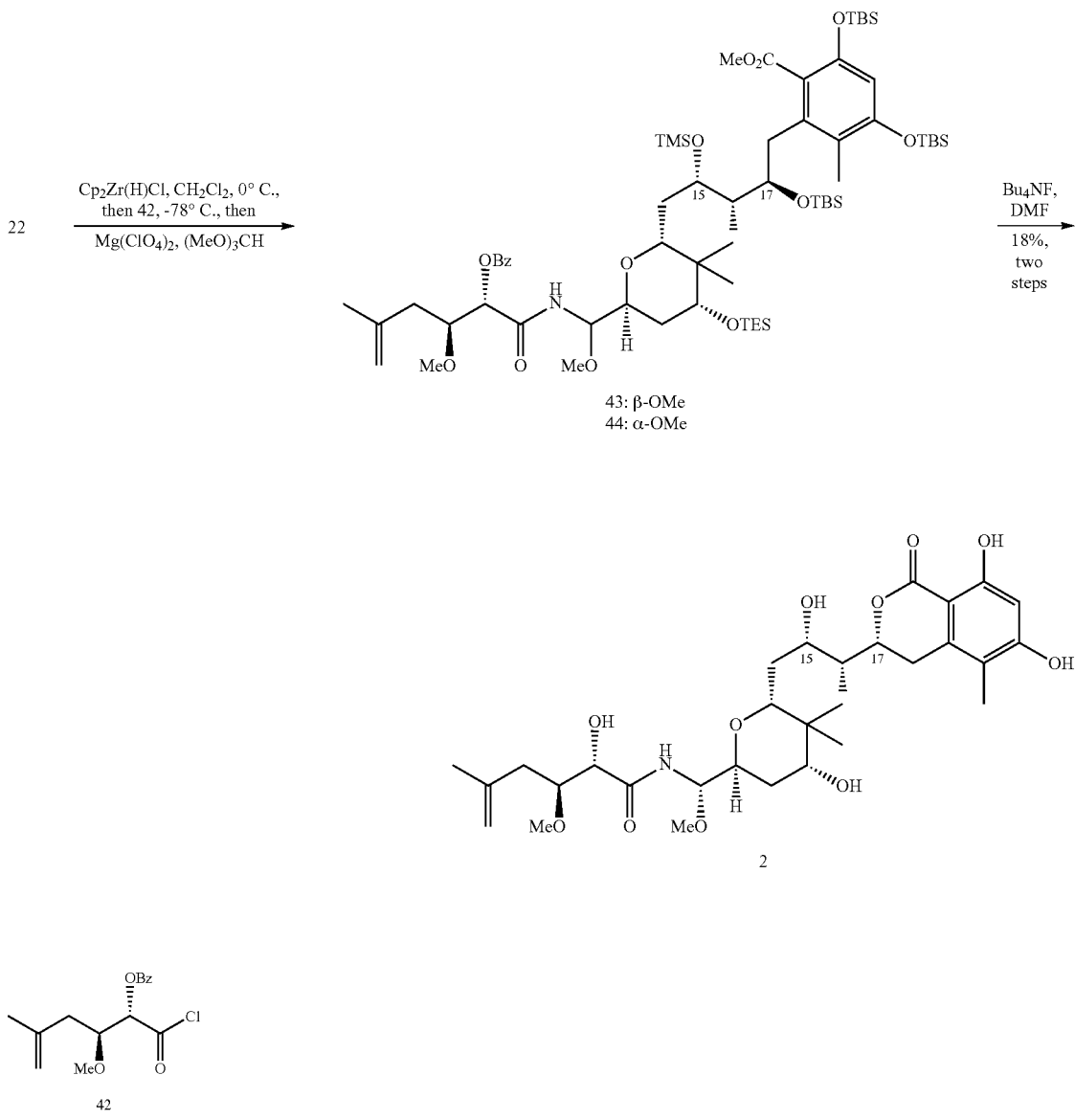

Scheme 8. Completion of the psymberin synthesis.

The availability of the left and right fragments for pederin and psymberin led us to undertake the synthesis of chimeric structures. We prepared a new analog that contains the left fragment of pederin and the right fragment of psymberin (Scheme 9 below). The multicomponent reaction employed nitrile 22 and acid chloride 33. MeOH was a suitable nucleophile in this reaction since stereocontrol did not prove to be a problem when 2 eq $Mg(ClO_4)_2$ were employed. Crude product 45 was subjected to $Bu_4NF$ in DMF to cleave the silyl ethers and form the dihydroisocoumarin unit. The benzoate ester was only partially cleaved under these conditions, in contrast to our observations with psymberin. The crude mixture was treated with LiOH in MeOH and $H_2O$ to complete the synthesis of chimera 46 that we have named pedestatin (pederin+irciniastatin).

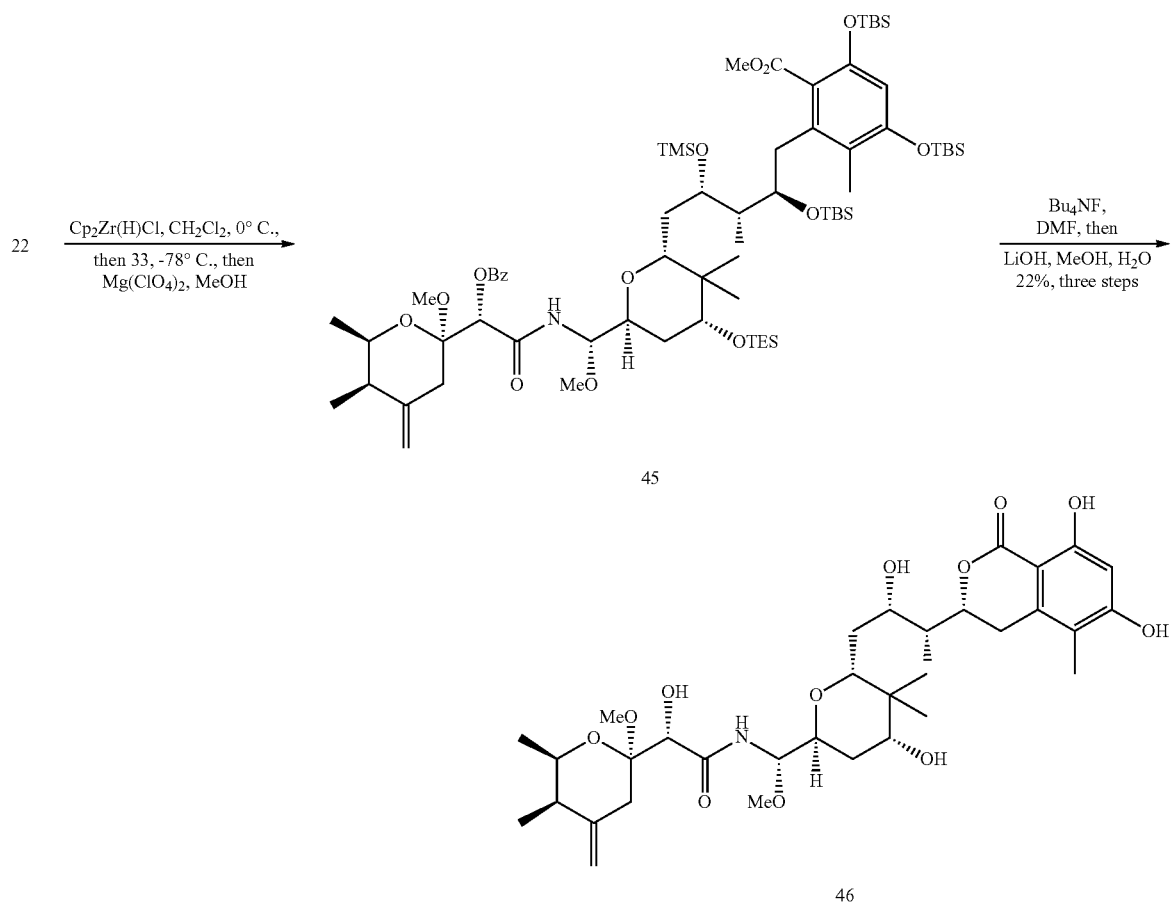

Scheme 9. Synthesis of the pederin-psymberin chimera pedestatin.

Cytotoxicity Studies

The potency of the above-described compounds was measured in cell viability studies using HCT116 colon cancer cells with an MTS assay with a three day incubation period. The results are shown in Table 1.

TABLE 1

$GI_{50}$ values of the natural products and analogs against HCT116 cells.

| entry | compound | description | GI50 (nM) |
|---|---|---|---|
| 1 | 1 | pederin | 0.6 ± 0.1 |
| 2 | 36b | 10-ethoxy pederin | 0.34 ± 0.08 |
| 3 | 36c | 10-trifluoroethoxy pederin | 0.55 ± 0.024 |
| 4 | 36d | 10-dimthoxybenzyloxy pederin | 0.32 ± 0.09 |
| 5 | 36e | 10-desmethoxy pederin | 7.7 ± 0.24 |
| 6 | 37 | pederin enamide | 27 ± 0.88 |
| 7 | 40 | C4-desmethylene pederin | 6.5 ± 0.8 |
| 8 | 41 | 13-O-methyl pederin | 0.084 ± 0.01 |
| 9 | — | 13-OTBS pederin | 3.1 ± 0.1 |
| 10 | 2 | psymberin | 0.052 ± 0.02 |
| 11 | 46 | pedestatin | 0.046 ± 0.03 |

These studies showed that all of the compounds in this series are potent antiproliferative agents. The identity of the alkoxy group in the acyl aminal subunit appears to exert little influence over the biological activity, but the presence of the alkoxy group enhances potency by at least one order of magnitude (entries 1-4 vs. entry 5). The most potent pederin analog contains a methyl ether at the C13 position rather than a hydroxyl group, suggesting that reducing hydrophilicty at that site is beneficial to activity. This has also been observed in psymberin analogs that lack a substituent at that position (Huang et al., Org. Lett. 2009, 11, 867). Dramatic increases to the size and hydrophobicity at the C13 position proved to be modestly detrimental activity, as seen in the TBS ether analog (isolated from an unsuccessful attempt at cleavage at the end of the sequence) in entry 9. Remarkably the enamide analog also showed reasonable activity (entry 6) despite the structural changes that result from changes to hybridization changes. The approximately one order of magnitude potency reduction of the des-methylene analog (entry 7), though consistent with results from the Nakata group, was somewhat surprising based on the minimal structural perturbation that this change effects on the hydrogen bond donors and acceptors in the molecule (Fukui et al., Bioorg. Med. Chem. Lett. 1997, 7, 2081). Psymberin is more potent than pederin (entries 1 and 10). While the GI50 value that we observed was somewhat lower than the value in the literature for this cell line (0.16 nM) the values were within a factor of three and were consistent over several assays. Chimera 46 is at least as potent and quite likely more potent than psymberin (entry 11). This result is quite significant in consideration of De Brabander's results, showing that a chimera that contained the left fragment of psymberin and the right fragment of pederin was not a potent cytotoxin (Xiang et al. Org. Lett. 2007, 9, 227). Our results suggest that pederin and psymberin share a common binding site on the ribosome and that the left fragment of pederin and the right fragment of psymberin are the essential components for the biological activity of these natural products. Compounds 1,36b-e, 37, 40, and 41 were tested against a p53 knockout variant of the HCT116 cell line and showed essentially identical activity. These results indicate that the apoptotic pathway is not dependent on p53.

Structural Basis for Biological Activity

The published crystal structure of the complex between mycalamide A and the large ribosomal subunit provides an opportunity to interpret the differences in biological activity among the molecules reported here (Gurel et al., Antimicrob. Agents Chemother 2009, 53, 5010). Such analysis may prove valuable in the design of second-generation analogs with improved activity. Given the fact that the structures of mycalamide A and pederin are closely related, we reasoned that the two natural products share similar binding modes. The coordinates published for mycalamide A in complex with the ribosome differ from the natural product by epimerization at C10. Since the prior study reported that material of natural origin was used in crystallization, we re-interpreted the published electron density using coordinates for the correct diastereomer. With the refined structure of the mycalamide A/ribosome complex in hand, pederin was docked into the binding site by superposition of the backbone atoms shared between the two molecules (FIG. 2). Analysis of the resulting model provides several insights into the structural basis for the biological activity of a variety of natural N-acyl aminal cytotoxins and their synthetic analogs.

The potency of 10-desmethoxy pederin (36e) was somewhat surprising in consideration of reports that related compounds that lack oxygenation or are epimeric at C10[9] show significantly diminished activity. An examination of the bioactive conformation of pederin in the bound structure suggests multiple roles for oxygenation at C10 (FIG. 3). Foremost, the C10 alkoxy group promotes a conformation about the C10-C11 bond that matches the ribosome-bound structure by forcing the less bulky C10-hydrogen to occupy the position over the tetrahydropyran ring (FIG. 3A). Evidence for presence of this conformational preorganization in solution is provided by the large coupling constant (~8 Hz) between the C10 and C11 hydrogens in the 1H NMR spectrum of pederin. Epimerization at C10 forces the amide group into an unproductive binding orientation in order to relieve the energetic penalty of placing the methoxy group over the tetrahydropyran ring. The 10-deoxy compound lacks a conformational bias around the C10-C11 bond; this loss of conformational preorganization may contribute to the weaker binding observed for 10-desmethoxy pederin compared to the natural product.

Two other features around C10 in the model for pederin bound to the ribosome are noteworthy. The binding region for the C10 methoxy group appears capable of accommodating larger substituents (FIG. 3B), in accord with our observation that larger alkoxy groups do not reduce activity. The structure also shows a hydrogen bond between the oxygen at C10 and the amino group of a nearby guanine residue (FIG. 3C). Thus, the role of the alkoxy group may transcend simple conformational restriction by providing direct contacts that enhance binding affinity. Collectively, the results of our structural analysis provide a picture of the role of the C10 substituent that is consistent with available biological data for pederin and its analogs. Closer examinations of the known natural products that lack oxygen at the C10 position reveal the presence of other structural perturbations that are the likely source of their diminished biological activity.

Figure 4:
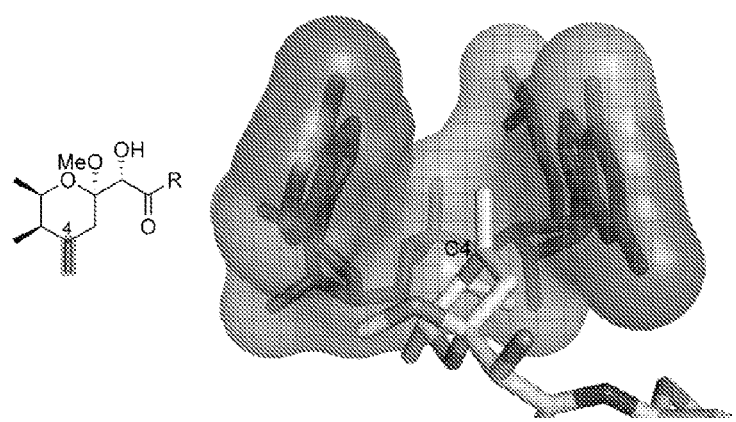
FIG. 4. The exocyclic alkene at C4 in the left-hand fragment of pederin intercalates between two sequential bases in the ribosome.

The origin of the strong influence of the pederic acid component on pederin bioactivity, and the exocyclic alkene in particular, can be proposed based on the bound structure. In the model of the pederin/ribosome complex, the exocyclic alkene of the pederic acid ring intercalates between adjacent adenine and guanine residues in the binding pocket (FIG. 4). We propose that this interaction acts as an anchor that orients other functional groups of the acyl fragment. Deletion of the exocyclic methylene (as in 40) or removal of ring conformational restraints (as in psymberic acid) attenuates the binding contribution of the acyl fragment and reduces activity. The pocket between the nucleobases appears sufficiently large to accommodate the products of exocyclic alkene reduction, which have been shown to retain cytotoxic activity.

The lack of hydrogen-bonding contacts involving the C13 hydroxyl group suggests that it serves no role in ribosome binding. This is consistent with results from the Schering group showing that deoxygenation at the corresponding position of psymberin actually increased activity. Replacement of the C13 hydroxyl group in pederin with a methyl ether led to the most cytotoxic analog (41) among those we tested. Taken together, these observations suggest that increasing the hydrophobicity at C13 may be a general strategy to enhance potency in this family of natural products.

Figure 5:
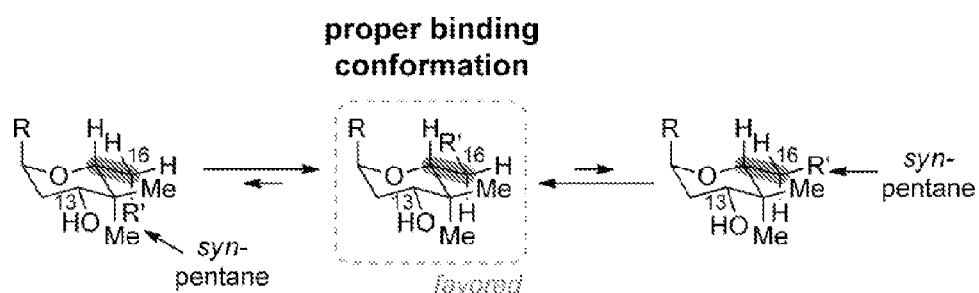
FIG. 5. The geminal methyl groups in the right-hand tetrahydropyran ring in pederin restrict rotation about C15-C16 and thereby the orientation of the branched side chain (R').

We propose that the geminal methyl groups at C14 set the orientation of the branched side chain projecting off the right fragment of pederin (FIG. 5). Conformational constraint of the C15-C16 bond arises from the minimization of the syn-pentane interactions that would be present in conformations that are not relevant for binding. The existence of this conformational constraint in solution is supported by observed 1H NMR coupling constants of 10.4 and 1.8 Hz for the C15 hydrogen that indicate a rigid conformation with one anti- and one gauche relationship to the hydrogens on C16. Thus, the tetrahydropyran ring appears to serve as a scaffold to align the left and right arms into the proper binding orientation.

Figure 6:
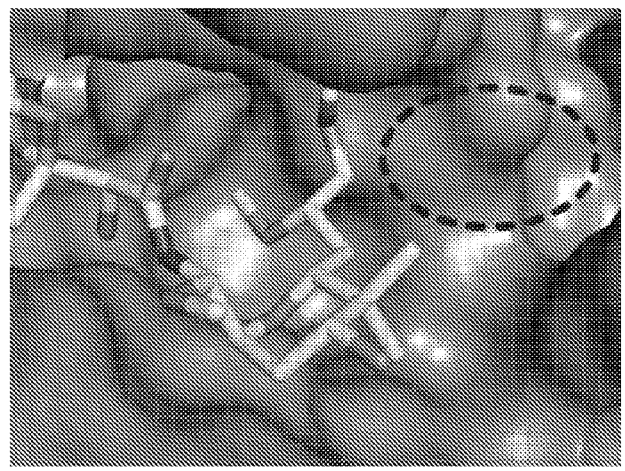
FIG. 6. An unoccupied pocket adjacent to the right-hand fragment of pederin suggests a possible basis for the enhanced efficacy of psymberin and pedestatin.

Although we have no information regarding the bound conformation of psymberin, we note the presence of a sizable cavity adjacent to the end of the right fragment of pederin (FIG. 6) that could accommodate the dihydroisocoumarin group of psymberin and the long chain of the structurally-related onnamides. Further crystallographic studies are required to determine the precise structural basis for the potency enhancement that the dihydroisocoumarin group effects.

Second Generation Analogs

The results from the initial round of biological assays and the structural details that were gleaned from the modeling studies provide a basis for the design and synthesis of a second wave of analogs. These compounds were designed to test hypotheses regarding ribosome binding and/or to facilitate synthesis.

The respectable activity that C10-desmethoxy analog 36e effects led us to consider other analogs that lack oxygenation at the C10 site (C8 site of psymberin). Since 36e was formed from side-products of the multicomponent reaction we changed the route so that the nitrile was reduced to a primary amine followed by conventional amide coupling (Scheme 10 below). The reduction of nitrile 22 proceeded with $H_2$ (1 atm) in the presence of a mixture of Pd/C and $PtO_2$ in HOAc and EtOAc to provide the corresponding amine. Coupling the crude amine to psymberic acid derivative 32 with EDC and HOBt led to the amide, which was treated with $Bu_4NF$ in DMF to yield 8-desmethoxy psymberin, 47. The yield was 47% for the three step sequence in which no purification of the intermediates was required. A similar sequence was executed with pederic acid derivative 27. An additional step was required to complete the cleavage of the sterically hindered benzoate group, similar to the synthesis of chimera 46. Through this route 10-desmethoxy pedestain 48 was prepared, again in 47% overall yield and with no intermediate purification. We also constructed a pederin analog that lacks the C4 alkene and the C10 methoxy group to facilitate synthesis and handling, and contains the C13 methyl ether to compensate for the potency loss that these changes would accrue. Reduction of nitrile 12b followed by coupling of the resulting amine with desmethylene pederic acid derivative 29 in the presence of EDC and HOBt provided the desired amide in 65% yield. Cleavage of the benzoate group provided the desired analog in 87% yield.

Scheme 10. Synthesis of desmethoxy analogs.

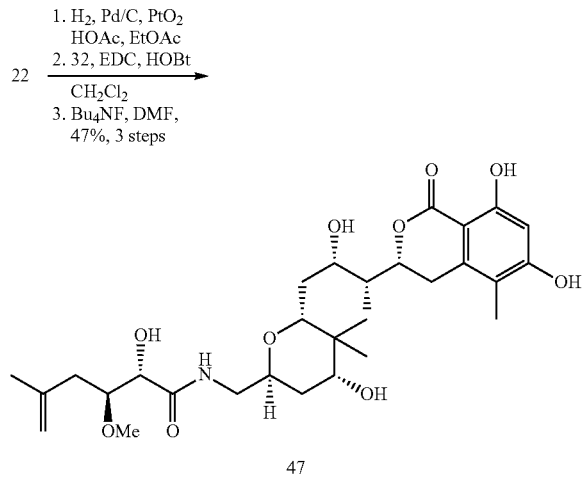

47

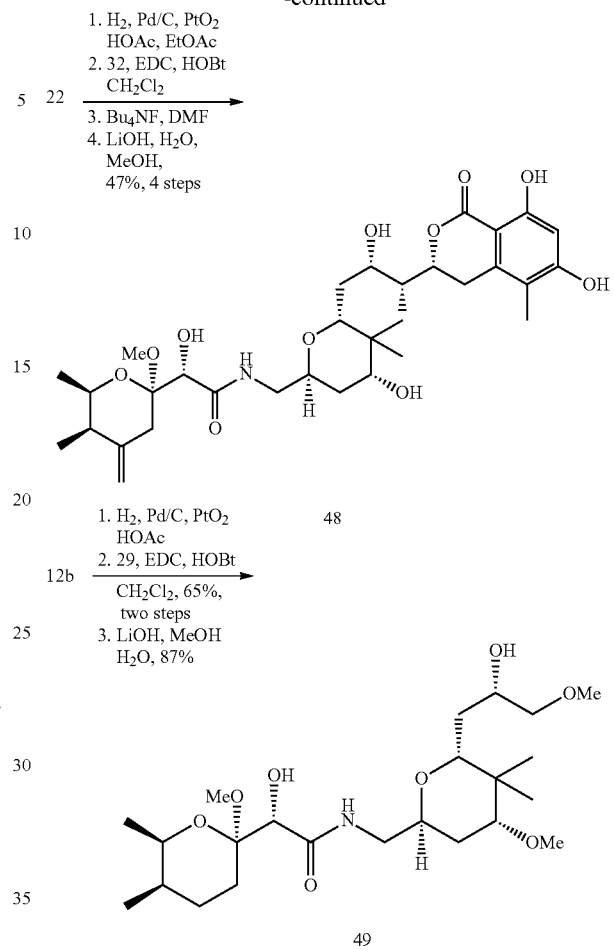

The final set of analogs was designed to test our hypotheses regarding the importance of conformation constraint and a hydrogen bonding interaction between the C10 methoxy group and the ribosome. This was achieved by replacing the methoxy group with a methyl group (Scheme 11). Exposing nitrile 12b to MeMgBr followed by quenching with MeOH and reducing the resulting imine with $NaBH_4$ provided amine 50 as an inseparable 1.5:1 mixture of diastereomers (as determined by NMR). Acylation of the mixture with acid 29 followed by benzoate cleavage with LiOH provided methyl analogs 51 and 52 in 31% and 26% yields, respectively, for the three step sequence.

Scheme 11. Synthesis of alkyl branched amide analogs.

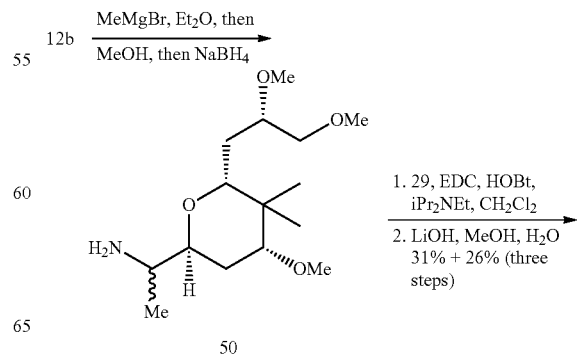

-continued

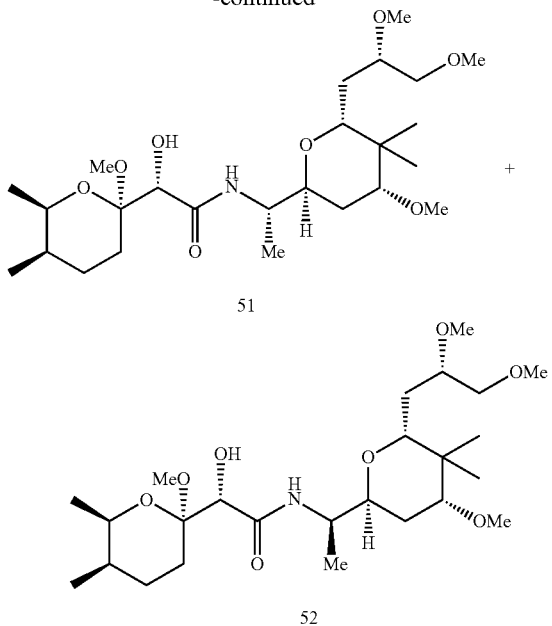

51

52

Biological Evaluation of Second Generation Analogs

The second generation analogs were evaluated for their ability to inhibit HCT116 cell growth through the same protocol that was used to evaluate the initial set of compounds. The results are shown in Table 2.

TABLE 2

$GI_{50}$ values for second generation analogs.

| entry | compound | description | $GI_{50}$ |
|---|---|---|---|
| 1 | 47 | 8-desmethoxy psymberin | 0.83 ± 0.1 nM |
| 2 | 48 | 10-desmethoxy pedestatin | 0.068 ± 0.02 nM |
| 3 | 49 | 4-desmethylene-10-desmethoxy 13-O-methylpederin | 79 ± 8 nM |
| 4 | 51 | 4-desmethylene-10-(S)-methyl 13-O-methylpederin | 42 ± 5 nM |
| 5 | 52 | 4-desmethylene-10-(R)-methyl 13-O-methylpederin | >9000 nM |

Pharmaceutical Compositions

Another aspect of the disclosure includes pharmaceutical compositions prepared for administration to a subject and which include a therapeutically effective amount of one or more of the compounds disclosed herein. In certain embodiments, the pharmaceutical compositions are useful for treating a neoplasm, particularly cancer. The therapeutically effective amount of a disclosed compound will depend on the route of administration, the species of subject and the physical characteristics of the subject being treated. Specific factors that can be taken into account include disease severity and stage, weight, diet and concurrent medications. The relationship of these factors to determining a therapeutically effective amount of the disclosed compounds is understood by those of skill in the art.

Pharmaceutical compositions for administration to a subject can include at least one further pharmaceutically acceptable additive such as carriers, thickeners, diluents, buffers, preservatives, surface active agents and the like in addition to the molecule of choice. Pharmaceutical compositions can also include one or more additional active ingredients such as antimicrobial agents, anti-inflammatory agents, anesthetics, and the like. The pharmaceutically acceptable carriers useful for these formulations are conventional. *Remington's Pharmaceutical Sciences*, by E. W. Martin, Mack Publishing Co., Easton, Pa., 19th Edition (1995), describes compositions and formulations suitable for pharmaceutical delivery of the compounds herein disclosed.

In general, the nature of the carrier will depend on the particular mode of administration being employed. For instance, parenteral formulations usually contain injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutical compositions disclosed herein include those formed from pharmaceutically acceptable salts and/or solvates of the disclosed compounds. Pharmaceutically acceptable salts include those derived from pharmaceutically acceptable inorganic or organic bases and acids. Particular disclosed compounds possess at least one basic group that can form acid-base salts with acids. Examples of basic groups include, but are not limited to, amino and imino groups. Examples of inorganic acids that can form salts with such basic groups include, but are not limited to, mineral acids such as hydrochloric acid, hydrobromic acid, sulfuric acid or phosphoric acid. Basic groups also can form salts with organic carboxylic acids, sulfonic acids, sulfo acids or phospho acids or N-substituted sulfamic acid, for example acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid, and, in addition, with amino acids, for example with α-amino acids, and also with methanesulfonic acid, ethanesulfonic acid, 2-hydroxymethanesulfonic acid, ethane-1,2-disulfonic acid, benzenedisulfonic acid, 4-methylbenzenesulfonic acid, naphthalene-2-sulfonic acid, 2- or 3-phosphoglycerate, glucose-6-phosphate or N-cyclohexylsulfamic acid (with formation of the cyclamates) or with other acidic organic compounds, such as ascorbic acid. In particular, suitable salts include those derived from alkali metals such as potassium and sodium, alkaline earth metals such as calcium and magnesium, among numerous other acids well known in the pharmaceutical art.

Certain compounds include at least one acidic group that can form an acid-base salt with an inorganic or organic base. Examples of salts formed from inorganic bases include salts of the presently disclosed compounds with alkali metals such as potassium and sodium, alkaline earth metals, including calcium and magnesium and the like. Similarly, salts of acidic compounds with an organic base, such as an amine (as used herein terms that refer to amines should be understood to include their conjugate acids unless the context clearly indicates that the free amine is intended) are contemplated, including salts formed with basic amino acids, aliphatic amines, heterocyclic amines, aromatic amines, pyridines, guanidines and amidines. Of the aliphatic amines, the acyclic aliphatic amines, and cyclic and acyclic di- and tri-alkyl amines are particularly suitable for use in the disclosed compounds. In addition, quaternary ammonium counterions also can be used.

Particular examples of suitable amine bases (and their corresponding ammonium ions) for use in the present compounds include, without limitation, pyridine, N,N-dimethylaminopyridine, diazabicyclononane, diazabicycloundecene, N-methyl-N-ethylamine, diethylamine, triethylamine, diisopropylethylamine, mono-, bis- or tris-(2-hydroxyethyl) amine, 2-hydroxy-tert-butylamine, tris(hydroxymethyl)methylamine, N,N-dimethyl-N-(2-hydroxyethyl)amine, tri-(2-hydroxyethyl)amine and N-methyl-D-glucamine. For additional examples of "pharmacologically acceptable salts," see Berge et al., *J. Pharm. Sci.* 66:1 (1977).

Compounds disclosed herein can be crystallized and can be provided in a single crystalline form or as a combination of different crystal polymorphs. As such, the compounds can be provided in one or more physical form, such as different crystal forms, crystalline, liquid crystalline or non-crystalline (amorphous) forms. Such different physical forms of the compounds can be prepared using, for example different solvents or different mixtures of solvents for recrystallization. Alternatively or additionally, different polymorphs can be prepared, for example, by performing recrystallizations at different temperatures and/or by altering cooling rates during recrystallization. The presence of polymorphs can be determined by X-ray crystallography, or in some cases by another spectroscopic technique, such as solid phase NMR spectroscopy, IR spectroscopy, or by differential scanning calorimetry.

The pharmaceutical compositions can be administered to subjects by a variety of mucosal administration modes, including by oral, rectal, intranasal, intrapulmonary, or transdermal delivery, or by topical delivery to other surfaces. Optionally, the compositions can be administered by non-mucosal routes, including by intramuscular, subcutaneous, intravenous, intra-arterial, intra-articular, intraperitoneal, intrathecal, intracerebroventricular, or parenteral routes. In other alternative embodiments, the compound can be administered ex vivo by direct exposure to cells, tissues or organs originating from a subject.

To formulate the pharmaceutical compositions, the compound can be combined with various pharmaceutically acceptable additives, as well as a base or vehicle for dispersion of the compound. Desired additives include, but are not limited to, pH control agents, such as arginine, sodium hydroxide, glycine, hydrochloric acid, citric acid, and the like. In addition, local anesthetics (for example, benzyl alcohol), isotonizing agents (for example, sodium chloride, mannitol, sorbitol), adsorption inhibitors (for example, Tween 80 or Miglyol 812), solubility enhancing agents (for example, cyclodextrins and derivatives thereof), stabilizers (for example, serum albumin), and reducing agents (for example, glutathione) can be included. Adjuvants, such as aluminum hydroxide (for example, Amphogel, Wyeth Laboratories, Madison, N.J.), Freund's adjuvant, MPL™ (3-O-deacylated monophosphoryl lipid A; Corixa, Hamilton, Ind.) and IL-12 (Genetics Institute, Cambridge, Mass.), among many other suitable adjuvants well known in the art, can be included in the compositions. When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of about 0.3 to about 3.0, such as about 0.5 to about 2.0, or about 0.8 to about 1.7.

The compound can be dispersed in a base or vehicle, which can include a hydrophilic compound having a capacity to disperse the compound, and any desired additives. The base can be selected from a wide range of suitable compounds, including but not limited to, copolymers of polycarboxylic acids or salts thereof, carboxylic anhydrides (for example, maleic anhydride) with other monomers (for example, methyl (meth)acrylate, acrylic acid and the like), hydrophilic vinyl polymers, such as polyvinyl acetate, polyvinyl alcohol, polyvinylpyrrolidone, cellulose derivatives, such as hydroxymethylcellulose, hydroxypropylcellulose and the like, and natural polymers, such as chitosan, collagen, sodium alginate, gelatin, hyaluronic acid, and nontoxic metal salts thereof. Often, a biodegradable polymer is selected as a base or vehicle, for example, polylactic acid, poly(lactic acid-glycolic acid) copolymer, polyhydroxybutyric acid, poly(hydroxybutyric acid-glycolic acid) copolymer and mixtures thereof. Alternatively or additionally, synthetic fatty acid esters such as polyglycerin fatty acid esters, sucrose fatty acid esters and the like can be employed as vehicles. Hydrophilic polymers and other vehicles can be used alone or in combination, and enhanced structural integrity can be imparted to the vehicle by partial crystallization, ionic bonding, cross-linking and the like. The vehicle can be provided in a variety of forms, including fluid or viscous solutions, gels, pastes, powders, microspheres and films for direct application to a mucosal surface.

The compound can be combined with the base or vehicle according to a variety of methods, and release of the compound can be by diffusion, disintegration of the vehicle, or associated formation of water channels. In some circumstances, the compound is dispersed in microcapsules (microspheres) or nanocapsules (nanospheres) prepared from a suitable polymer, for example, isobutyl 2-cyanoacrylate (see, for example, Michael et al., *J. Pharmacy Pharmacol.* 43:1-5, 1991), and dispersed in a biocompatible dispersing medium, which yields sustained delivery and biological activity over a protracted time.

The compositions of the disclosure can alternatively contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate. For solid compositions, conventional nontoxic pharmaceutically acceptable vehicles can be used which include, for example, pharmaceutical grades of mannitol, lactose, starch, magnesium stearate, sodium saccharin, talcum, cellulose, glucose, sucrose, magnesium carbonate, and the like.

Pharmaceutical compositions for administering the compound can also be formulated as a solution, microemulsion, or other ordered structure suitable for high concentration of active ingredients. The vehicle can be a solvent or dispersion medium containing, for example, water, ethanol, polyol (for example, glycerol, propylene glycol, liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols, such as mannitol and sorbitol, or sodium chloride in the composition. Prolonged absorption of the compound can be brought about by including in the composition an agent which delays absorption, for example, monostearate salts and gelatin.

In certain embodiments, the compound can be administered in a time release formulation, for example in a composition which includes a slow release polymer. These compositions can be prepared with vehicles that will protect against rapid release, for example a controlled release vehicle such as a polymer, microencapsulated delivery system or bioadhesive gel. Prolonged delivery in various compositions of the disclosure can be brought about by including in the composition agents that delay absorption, for example, aluminum monostearate hydrogels and gelatin. When controlled release formulations are desired, controlled release binders suitable for use in accordance with the disclosure include any biocompatible controlled release material which is inert to the active agent and which is capable of incorporating the compound and/or other biologically active agent. Numerous such materials are known in the art. Useful controlled-release binders are materials that are metabolized slowly under physiological conditions following their delivery (for example, at a mucosal surface, or in the presence of bodily fluids). Appropriate binders include, but are not limited to, biocompatible polymers and copolymers well known in the art for use in sustained release formulations. Such biocompatible compounds are non-toxic and inert to surrounding tissues, and do not trigger significant adverse side effects, such as nasal irritation, immune response, inflammation, or the like. They are metabolized into metabolic products that are also biocompatible and easily eliminated from the body.

Exemplary polymeric materials for use in the present disclosure include, but are not limited to, polymeric matrices derived from copolymeric and homopolymeric polyesters having hydrolyzable ester linkages. A number of these are known in the art to be biodegradable and to lead to degradation products having no or low toxicity. Exemplary polymers include polyglycolic acids and polylactic acids, poly(DL-lactic acid-co-glycolic acid), poly(D-lactic acid-co-glycolic acid), and poly(L-lactic acid-co-glycolic acid). Other useful biodegradable or bioerodable polymers include, but are not limited to, such polymers as poly(epsilon-caprolactone), poly(epsilon-aprolactone-CO-lactic acid), poly(epsilon.-aprolactone-CO-glycolic acid), poly(beta-hydroxy butyric acid), poly(alkyl-2-cyanoacrilate), hydrogels, such as poly(hydroxyethyl methacrylate), polyamides, poly(amino acids) (for example, L-leucine, glutamic acid, L-aspartic acid and the like), poly(ester urea), poly(2-hydroxyethyl DL-aspartamide), polyacetal polymers, polyorthoesters, polycarbonate, polymaleamides, polysaccharides, and copolymers thereof. Many methods for preparing such formulations are well known to those skilled in the art (see, for example, *Sustained and Controlled Release Drug Delivery Systems*, J. R. Robinson, ed., Marcel Dekker, Inc., New York, 1978). Other useful formulations include controlled-release microcapsules (U.S. Pat. Nos. 4,652,441 and 4,917,893), lactic acid-glycolic acid copolymers useful in making microcapsules and other formulations (U.S. Pat. Nos. 4,677,191 and 4,728,721) and sustained-release compositions for water-soluble peptides (U.S. Pat. No. 4,675,189).

The pharmaceutical compositions of the disclosure typically are sterile and stable under conditions of manufacture, storage and use. Sterile solutions can be prepared by incorporating the compound in the required amount in an appropriate solvent with one or a combination of ingredients enumerated herein, as required, followed by filtered sterilization. Generally, dispersions are prepared by incorporating the compound and/or other biologically active agent into a sterile vehicle that contains a basic dispersion medium and the required other ingredients from those enumerated herein. In the case of sterile powders, methods of preparation include vacuum drying and freeze-drying which yields a powder of the compound plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like.

In accordance with the various treatment methods of the disclosure, the compound can be delivered to a subject in a manner consistent with conventional methodologies associated with management of the disorder for which treatment or prevention is sought. In accordance with the disclosure herein, a prophylactically or therapeutically effective amount of the compound and/or other biologically active agent is administered to a subject in need of such treatment for a time and under conditions sufficient to prevent, inhibit, and/or ameliorate a selected disease or condition or one or more symptom(s) thereof.

The administration of the compound of the disclosure can be for either prophylactic or therapeutic purpose. When provided prophylactically, the compound is provided in advance of any symptom. The prophylactic administration of the compound serves to prevent or ameliorate any subsequent disease process. When provided therapeutically, the compound is provided at (or shortly after) the onset of a symptom of disease or infection.

For prophylactic and therapeutic purposes, the compound can be administered to the subject by the oral route or in a single bolus delivery, via continuous delivery (for example, continuous transdermal, mucosal or intravenous delivery) over an extended time period, or in a repeated administration protocol (for example, by an hourly, daily or weekly, repeated administration protocol). The therapeutically effective dosage of the compound can be provided as repeated doses within a prolonged prophylaxis or treatment regimen that will yield clinically significant results to alleviate one or more symptoms or detectable conditions associated with a targeted disease or condition as set forth herein. Determination of effective dosages in this context is typically based on animal model studies followed up by human clinical trials and is guided by administration protocols that significantly reduce the occurrence or severity of targeted disease symptoms or conditions in the subject. Suitable models in this regard include, for example, murine, rat, avian, porcine, feline, non-human primate, and other accepted animal model subjects known in the art. Alternatively, effective dosages can be determined using in vitro models. Using such models, only ordinary calculations and adjustments are required to determine an appropriate concentration and dose to administer a therapeutically effective amount of the compound (for example, amounts that are effective to alleviate one or more symptoms of a targeted disease). In alternative embodiments, an effective amount or effective dose of the compound may simply inhibit or enhance one or more selected biological activities correlated with a disease or condition, as set forth herein, for either therapeutic or diagnostic purposes.

The actual dosage of the compound will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the compound for eliciting the desired activity or biological response in the subject. Dosage regimens can be adjusted to provide an optimum prophylactic or therapeutic response. A therapeutically effective amount is also one in which any toxic or detrimental side effects of the compound and/or other biologically active agent is outweighed in clinical terms by therapeutically beneficial effects. A non-limiting range for a therapeutically effective amount of a compound and/or other biologically active agent within the methods and formulations of the disclosure is about 0.01 mg/kg body weight to about 20 mg/kg body weight, such as about 0.05 mg/kg to about 5 mg/kg body weight, or about 0.2 mg/kg to about 2 mg/kg body weight.

Dosage can be varied by the attending clinician to maintain a desired concentration at a target site (for example, the lungs or systemic circulation). Higher or lower concentrations can be selected based on the mode of delivery, for example, transepidermal, rectal, oral, pulmonary, or intranasal delivery versus intravenous or subcutaneous delivery. Dosage can also be adjusted based on the release rate of the administered formulation, for example, of an intrapulmonary spray versus powder, sustained release oral versus injected particulate or transdermal delivery formulations, and so forth.

The compounds disclosed herein may also be co-administered with an additional therapeutic agent. Such agents include, but are not limited to, an anti-inflammatory agent, a matrix metalloprotease inhibitor, a lipoxygenase inhibitor, a cytokine antagonist, an immunosuppressant, an anti-cancer agent, an anti-viral agent, a cytokine, a growth factor, an immunomodulator, a prostaglandin or an anti-vascular hyperproliferation compound.

The instant disclosure also includes kits, packages and multi-container units containing the herein described pharmaceutical compositions, active ingredients, and/or means for administering the same for use in the prevention and treatment of diseases and other conditions in mammalian subjects. Kits for diagnostic use are also provided. In one embodiment, these kits include a container or formulation that contains one or more of the compounds described herein. In one example, this component is formulated in a pharmaceutical preparation for delivery to a subject. The compound is optionally contained in a bulk dispensing container or unit or multi-unit dosage form. Optional dispensing means can be provided, for example a pulmonary or intranasal spray applicator. Packaging materials optionally include a label or instruction indicating for what treatment purposes and/or in what manner the pharmaceutical agent packaged therewith can be used.

Certain embodiments are described in the following numbered paragraphs:

1. A compound, or a pharmaceutically acceptable salt, ester or solvate thereof, having a formula of:

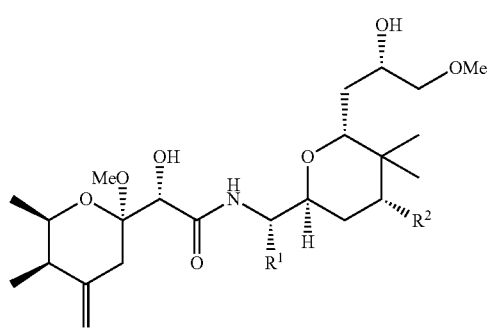

wherein at least one of $R^1$ or $R^2$ includes a linker that includes a reactive functional group that can bind to a targeting moiety; or a formula of:

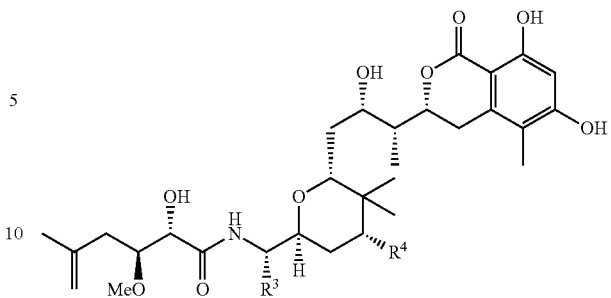

wherein at least one of $R^3$ or $R^4$ includes a linker that includes a reactive functional group that can bind to a targeting moiety; or a formula of:

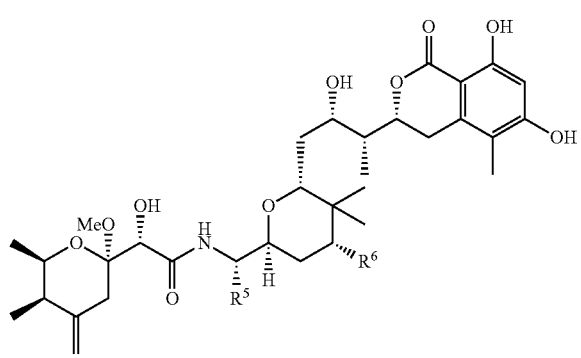

wherein at least one of $R^5$ or $R^6$ includes a linker that includes a reactive functional group that can bind to a targeting moiety.

2. A compound, or a pharmaceutically acceptable salt, ester or solvate thereof, having a formula of:

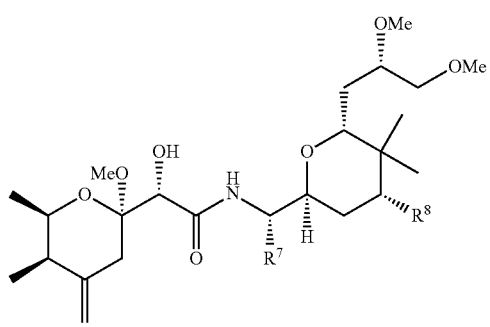

wherein at least one of $R^7$ or $R^8$ includes a structure of -L-T, wherein L is a linker and T is a targeting moiety; or a formula of:

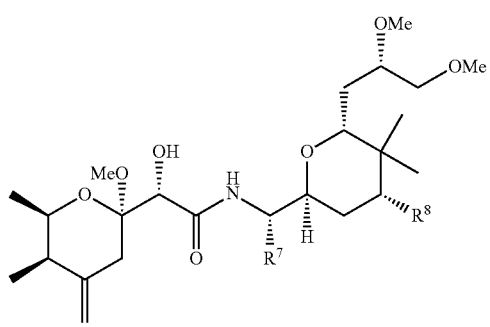

wherein at least one of $R^9$ or $R^{10}$ includes a structure of -L-T, wherein L is a linker and T is a targeting moiety; or a formula of:

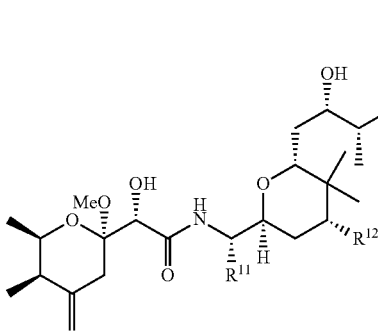

wherein at least one of $R^{11}$ or $R^{12}$ includes a structure of -L-T, wherein L is a linker and T is a targeting moiety.

3. A compound, or a pharmaceutically acceptable salt, ester or solvate thereof, comprising:

A-L wherein A comprises pederin, a pederin analog, psymberin, a psymberin analog, or a pederin/psymberin chimera; and L comprises a linker that includes a reactive functional group that can bind to a targeting moiety, wherein L is bonded at C10 and/or C13 position of pederin, the pederin analog or the pederin/psymberin chimera, or L is bonded at C8 and/or C11 position of psymberin or the psymberin analog.

4. The compound of paragraph 1 wherein at least one of $R^1$ or $R^2$ has the structure —O-L wherein O is an oxygen atom and L is a linker, or at least one of $R^3$ or $R^4$ has the structure —O-L wherein O is an oxygen atom and L is a linker, or at least one of $R^5$ or $R^6$ has the structure —O-L wherein O is an oxygen atom and L is a linker.

5. The compound of paragraph 2, wherein at least one of $R^7$ or $R^8$ has a structure of —O-L-T wherein O is an oxygen atom, L is the linker and T is the targeting moiety, or at least one of $R^9$ or $R^{10}$ has a structure of —O-L-T wherein O is an oxygen atom, L is the linker and T is the targeting moiety, or at least one of $R^{11}$ or $R^{12}$ has a structure of —O-L-T wherein O is an oxygen atom, L is the linker and T is the targeting moiety.

6. The compound of any one of paragraphs 1 to 5, wherein the linker includes a divalent selected from an alkanediyl, a cycloalkanediyl, an aryldiyl, a heteroaryldiyl, or an alkanearyldiyl.

7. The compound of any of paragraphs 1 to 6, wherein the targeting moiety is selected from an antibody, a liposome, or a dendrimer.

8. The compound of any of paragraphs 1 to 6, wherein the targeting moiety comprises an antibody.

9. The compound of any one of paragraphs 1 or 3 to 8, wherein the reactive functional group is selected from an amine-reactive group, a thiol-reactive group, a carboxylate-reactive group, a hydroxyl reactive-group, an aldehyde- or ketone-reactive group, or an active hydrogen-reactive group.

10. The compound of any one of paragraphs 1 or 3 to 8, wherein the reactive functional group is selected from isothiocyanate, isocyanate, acyl azide, an N-hydroxysuccinimidyl ester, acid chloride, aldehyde, glyoxal, epoxide, oxirane, carbonate, imidoester, carbodiimide, haloacetyl, alkyl halide, maleimide, aziridine, acryloyl, pyridyl disulfide, TNB-thiol, diazoalkane, diazoacetyl, carbonyldiimidazole, carbonyldiimidazole, N,N'-disuccinimidyl carbonate, N-hydroxysuccinimidyl chloroformate, hydrazine, and diazonium.

11. A compound, or a pharmaceutically acceptable salt, ester or solvate thereof, having a formula of:

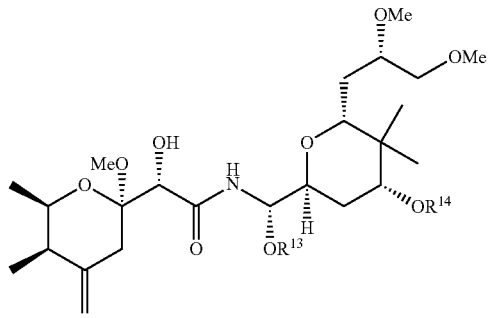

wherein $R^{13}$ is optionally substituted alkyl, and $R^{14}$ is H or optionally substituted alkyl, provided that if $R^{14}$ is H then $R^{13}$ is not methyl; or having a formula of:

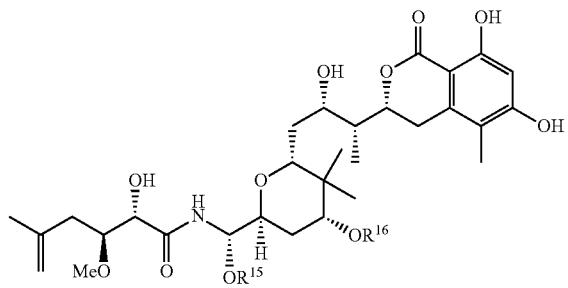

wherein $R^{15}$ is optionally substituted alkyl, and $R^{16}$ is H or optionally substituted alkyl, provided that if $R^{16}$ is H then $R^{14}$ is not methyl; or having a formula of:

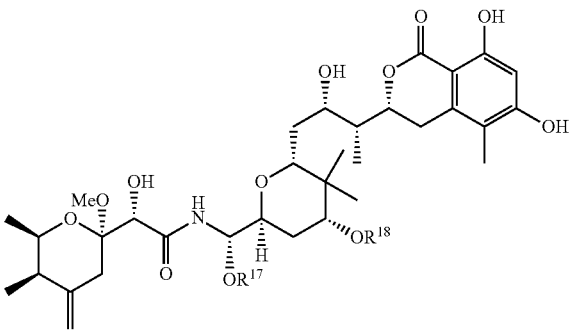

wherein $R^{17}$ is H or optionally substituted alkyl, and $R^{18}$ is H or optionally substituted alkyl.

12. The compound of paragraph 11, wherein at least one of $R^{13}$ or $R^{14}$ is a lower alkyl, a haloalkyl, or an aralkyl, or wherein at least one of $R^{15}$ or $R^{16}$ is a lower alkyl, a haloalkyl, or an aralkyl, or wherein at least one of $R^{17}$ or $R^{18}$ is a lower alkyl, a haloalkyl, or an aralkyl.

13. A pharmaceutical composition comprising at least one compound of any one of paragraphs 1 to 12, and at least one pharmaceutically acceptable additive.

14. A method for treating a neoplasm in a subject comprising administering to the subject at least one compound of any one of paragraphs 1 to 12.

15. The method of paragraph 14, wherein the neoplasm is cancer.

In view of the many possible embodiments to which the principles of the disclosed compounds, compositions and methods may be applied, it should be recognized that the illustrated embodiments are only preferred examples and should not be taken as limiting the scope of the invention.

What is claimed is:

1. A compound, or a pharmaceutically acceptable salt or ester thereof, comprising:

A-L wherein A comprises pederin, psymberin, or a pederin/psymberin chimera; and

L comprises a linker that includes a reactive functional group that can bind to a targeting moiety, wherein L is bonded at C10 and/or C13 position of pederin, or the pederin/psymberin chimera, or L is bonded at C8 and/or C11 position of psymberin, and wherein the linker includes a divalent radical selected from an alkanediyl, a cycloalkanediyl, an aryldiyl, a heteroaryldiyl, and an alkanearyldiyl.

2. The compound of claim 1, or a pharmaceutically acceptable salt or ester thereof, having a formula of:

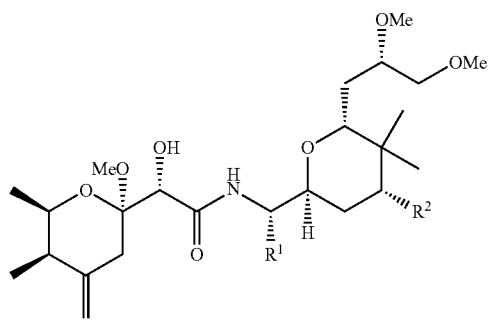

wherein at least one of $R^1$ or $R^2$ includes the linker that includes a reactive functional group that can bind to a targeting moiety; or a formula of:

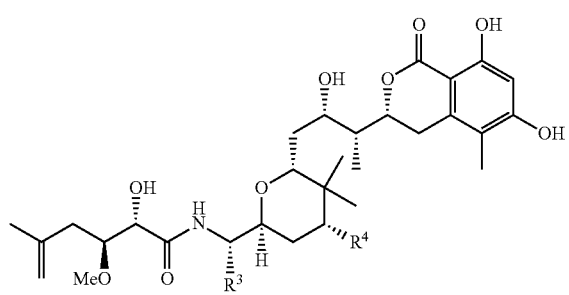

wherein at least one of $R^3$ or $R^4$ includes the linker that includes a reactive functional group that can bind to a targeting moiety; or a formula of:

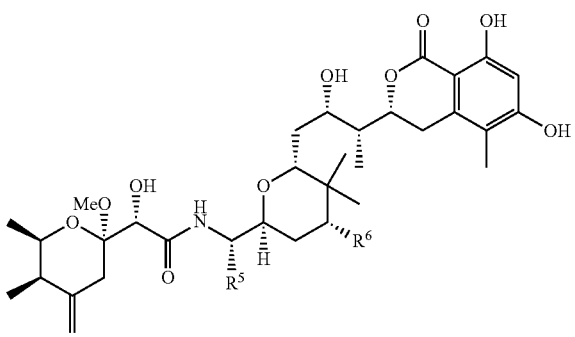

wherein at east one of $R^5$ or $R^6$ includes the linker that includes a reactive functional group that can bind to a targeting moiety wherein the linker in $R^1$, $R^2$, $R^3$, $R^4$, $R^5$ and $R^6$ includes a divalent radical selected from an alkanediyl, a cycloalkanediyl, an aryldiyl, a heteroaryldiyl and an alkanearyldiyl.

3. The compound of claim 2, wherein at least one of $R^1$ or $R^2$ has the structure —O-L wherein O is an oxygen atom and L is a linker, or at least one of $R^3$ or $R^4$ has the structure —O-L wherein O is an oxygen atom and L is a linker, or at least one of $R^5$ or $R^6$ has the structure —O-L wherein O is an oxygen atom and L is a linker.

4. The compound of claim 1, wherein the targeting moiety is an antibody, a liposome, or a dendrimer.

5. The compound of claim 1, wherein the reactive functional group is an amine-reactive group, a thiol-reactive group, a carboxylate-reactive group, a hydroxyl reactive-group, an aldehyde- or ketone-reactive group, or an active hydrogen-reactive group.

6. The compound of claim 1, wherein the reactive functional group is selected from isothiocyanate, isocyanate, acyl azide, an N-hydroxysuccinimidyl ester, acid chloride, aldehyde, glyoxal, epoxide, oxirane, carbonate, imidoester, carbodiimide, haloacetyl, alkyl halide, maleimide, aziridine, acryloyl, pyridyl disulfide, TNB-thiol, diazoalkane, diazoacetyl, carbonyldiimidazole, carbonyldiimidazole, N,N'-disuccinimidyl carbonate, N-hydroxysuccinimidyl chloroformate, hydrazine, and diazonium.

7. The compound of claim 3, wherein $R^1$ has the structure —O-L, and $R^2$ is an alkoxy methoxy.

8. The compound of claim 1, wherein $R^1$ has the structure —O-L, and the linker includes a divalent radical selected from an alkanediyl or a heteroaryldiyl.

9. The compound of claim 1, wherein the reactive functional group is a maleimide.

10. The compound of claim 3, wherein $R^1$ has the structure —O-L, the linker includes an alkanediyl coupled to a heteroaryldiyl, and reactive functional group includes a maleimide.

11. A pharmaceutical composition comprising at least one compound of claim 1, and at least one pharmaceutically acceptable additive.

12. A method for treating a neoplasm in a subject comprising administering to the subject at least one compound of claim 1.

13. The method of claim 12, wherein the neoplasm is cancer.

14. The method of claim 13, wherein the cancer is colon cancer.

15. The compound of claim 1, wherein L has the structure —O-linker.

16. The compound of claim 1, wherein the reactive functional group is olefin, acetylene, alcohol, phenol, ether, oxide, halide, aldehyde, ketone, carboxylic acid, ester, amide, cyanate, isocyanate, thiocyanate, isothiocyanate, amine, hydrazine, hydrazone, hydrazide, diazo, diazonium, nitro, nitrile, mercaptan, sulfide, disulfide, sulfoxide, sulfone, sulfonic acid, sulfinic acid, acetal, ketal, anhydride, sulfate, sulfenic acid, isonitrile, amidine, imide, imidate, nitrone, hydroxylamine, oxime, hydroxamic acid, thiohydroxamic acid, allene, ortho ester, sulfite, enamine, ynamine, urea, pseudourea, semicarbazide, carbodiimide, carbamate, imine, azide, azo, azoxy, or nitroso.

17. The compound of claim 16, wherein the reactive group is azide.

* * * * *